(12) United States Patent
Van Malderen et al.

(10) Patent No.: US 11,529,268 B2
(45) Date of Patent: Dec. 20, 2022

(54) ABSORBENT STRUCTURE COMPRISING RELEASE STRUCTURE

(71) Applicant: Drylock Technologies NV, Zele (BE)

(72) Inventors: Bart Van Malderen, Zele (BE); Werner Van Ingelgem, Zele (BE); Tom Derycke, Zele (BE); Steven Smet, Zele (BE)

(73) Assignee: Drylock Technologies NV, Zele (BE)

( * ) Notice: Subject to any disclaimer, the term of this patent is extended or adjusted under 35 U.S.C. 154(b) by 430 days.

(21) Appl. No.: 16/305,707

(22) PCT Filed: Apr. 3, 2017

(86) PCT No.: PCT/EP2017/057877
§ 371 (c)(1),
(2) Date: Nov. 29, 2018

(87) PCT Pub. No.: WO2017/207135
PCT Pub. Date: Dec. 7, 2017

(65) Prior Publication Data
US 2021/0030604 A1 Feb. 4, 2021

(30) Foreign Application Priority Data
May 31, 2016 (EP) .................................... 16447002

(51) Int. Cl.
*A61F 13/15* (2006.01)
*A61F 13/537* (2006.01)
(Continued)

(52) U.S. Cl.
CPC ...... *A61F 13/53704* (2013.01); *A61F 13/513* (2013.01); *A61F 13/51456* (2013.01);
(Continued)

(58) Field of Classification Search
CPC .............. A61F 13/53704; A61F 13/516; A61F 13/51456; A61F 13/53747;
(Continued)

(56) References Cited

U.S. PATENT DOCUMENTS

2008/0312628 A1 12/2008 Hundorf et al.
2019/0192354 A1* 6/2019 Bewick-Sonntag ........................ A61F 13/538

FOREIGN PATENT DOCUMENTS

EP 1526214 A1 4/2005
EP 2165015 A1 3/2010
(Continued)

OTHER PUBLICATIONS

"International Application No. PCT/EP2017/057877, International Search Report dated May 11, 2017", (dated May 11, 2017), 3 pgs.
(Continued)

*Primary Examiner* — Jacqueline F Stephens
(74) *Attorney, Agent, or Firm* — Schwegman Lundberg & Woessner, P.A.

(57) ABSTRACT

An absorbent article comprising a liquid pervious topsheet, a liquid impervious backsheet, and an absorbent structure positioned in between said topsheet and said backsheet, wherein the absorbent structure comprises an absorbent core positioned in between the topsheet and the backsheet, a release structure being positioned in fluid communication with the absorbent core, said absorbent core comprising little to no cellulose fibers and/or fluff pulp and said absorbent core comprising an absorbent polymer material for absorbing and permanently holding fluids received from the topsheet and the release structure, wherein said release structure comprises at least one fibrous substrate structure having the capacity to receive and temporarily hold the fluids in proximity to the absorbent core so that the fluids can
(Continued)

subsequently be transferred and released to and absorbed by the absorbent core.

20 Claims, 21 Drawing Sheets

(51) Int. Cl.
    *A61F 13/513* (2006.01)
    *A61F 13/514* (2006.01)
    *A61F 13/53* (2006.01)

(52) U.S. Cl.
    CPC .. *A61F 13/53747* (2013.01); *A61F 13/53752* (2013.01); *A61F 13/53756* (2013.01); *A61F 2013/530036* (2013.01); *A61F 2013/530343* (2013.01); *A61F 2013/530379* (2013.01); *A61F 2013/530737* (2013.01)

(58) Field of Classification Search
    CPC .......... A61F 13/53752; A61F 13/53756; A61F 2013/530036; A61F 2013/530379; A61F 2013/530737

See application file for complete search history.

(56) References Cited

FOREIGN PATENT DOCUMENTS

| | | |
|---|---|---|
| EP | 2992864 A1 | 3/2016 |
| WO | WO-9833464 A1 | 8/1998 |
| WO | WO-2005094748 A1 | 10/2005 |
| WO | WO-2013152809 A1 | 10/2013 |
| WO | WO-2013153235 A1 | 10/2013 |

OTHER PUBLICATIONS

"International Application No. PCT/EP2017/057877, Written Opinion dated May 11, 2017", (dated May 11, 2017), 6 pgs.

* cited by examiner

ABSORBENT STRUCTURE COMPRISING RELEASE STRUCTURE

TECHNICAL FIELD

The present invention pertains to the technical field of absorbent articles, more preferably disposable personal care articles such as diapers, baby pants, adult incontinent garments, feminine hygiene garments and the like, and to absorbent structures for use in such absorbent articles. More specifically the present invention relates to an absorbent structure comprising an overlying absorbent core containing little to no cellulose fibers or fluff pulp and an underlying and/or overlying release structure. This multilayer-layer absorbent structure is designed to improve the ability to absorb, distribute and retain fluids and consequently prevents excessive rewetting and leakage. The present invention also relates to an absorbent article comprising such absorbent structure and to a method and apparatus for manufacturing such absorbent structure.

BACKGROUND

Absorbent articles such as diapers, baby pants, adult incontinent garments and the like, typically comprise an absorbent core, positioned in between a liquid permeable or pervious, hydrophilic or semi hydrophilic topsheet and a liquid impermeable or impervious backsheet, which comprises an absorbent core comprising absorbent material that is able to absorb fluid and liquid bodily excretions of the user of the absorbent article and one or more superimposed acquisition and/or dispersion layers. The absorbent core is often held together by upper and/or lower nonwoven wrap layers.

On top of such absorbent cores often acquisition and dispersion layers are superimposed to enhance the uptake and transport of fluids and liquids excreted by the user. Typically the overlying acquisition layer is suitable to rapidly acquire the fluid and liquids from the user entering through the topsheet into the acquisition layer and subsequently transit the fluid and liquid into the underlying dispersion layer which is placed on top of the absorbent core. This dispersion layer further allows the liquid to migrate away from the article. The terms top, back, upper, lower, overlying, underlying, above, beneath, higher, lower and so on are referring to the relative positions of said layers with respect to one another within the absorbent article.

The absorbent material of an absorbent core is typically an absorbent particulate polymer material which is usually dispersed in a matrix of cellulose fibers or fluff pulp in order to prevent the particulate material from aggregating, as well as to prevent gel blocking. Gel blocking can occur when the absorbent particulate polymer material absorbs liquid, as they tend to typically swell and form a gel structure. This gel structure often blocks the further transfer of liquid into the remaining absorbent core. As a result, the liquid may be unable to reach the remaining absorbent particulate polymer material and the efficiency of the overall absorbent article decreases significantly.

Recent years however, there has been a strong demand for more flexible, thinner, light-weight, absorbent cores to resolve various problems associated with manufacturing, marketing, design, fit, wearing comfort, distribution, garbage disposal, material and energy consumption, transport and storage costs and the like. This lead to the search for and the development and production of absorbent articles of which the absorbent cores contains little to no cellulose fibers or fluff pulp, as the latter tend to be quite bulky, thus rendering generally more thick absorbent cores which reduces the overall wearing comfort of the user of the absorbent article.

However it was found that when using absorbent cores with little to no cellulose fibers or fluff pulp, significant problems occurred in relation to liquid uptake, absorption, transport and retention as to gel blocking. It has also been shown to be extremely difficult to fully, instantly and timely utilize the entire absorption, distribution and retention capacity of the absorbent article, often leading to dysfunctional absorbent structures, bad rewet values and overall failing absorbent articles. Even the traditionally known superimposed acquisition and dispersion layers could not resolve the drawbacks associated with these flexible and thin absorbent cores with little to no cellulose fibers or fluff pulp.

Hence, various absorbent cores containing little to no cellulose fibers or fluff pulp were developed in the past few years to try and overcome the above drawbacks, whereby the relative high amounts of absorbent polymer materials necessary to replace the absorption, distribution and retention capacity of the excluded cellulose fibers and/or fluff pulp were loaded, distributed and immobilized within these new absorbent cores according to several techniques. However given the ability and capacity of the absorbent core to absorb, transport and retain fluid and liquids is heavily dependent upon the form, position and/or manner wherein these absorbent polymer materials are incorporated within the absorbent core several drawback remained unsolved. In general the substantially heterogeneously distributed absorbent cores having non-continuous compartments and/or clusters of absorbent polymer material have in general proven to be better in coping with the above mentioned problems, nevertheless they also proved to remain unsatisfactory within most of the available absorbent articles. Especially problematic however, were the substantially homogenously distributed absorbent structures having continuous layers of absorbent polymer particulate material given they exhibit a substantially homogenous swollen absorbent polymer material area for second, third and next liquid insults wherein the dry and/or wetted absorbent polymer material layer may actually act as a liquid barrier. These problems and complications are especially prevalent within very flexible, thin, lightweight absorbent structures wherein high amounts of absorbent polymer material are distributed within the absorbent core of the absorbent article. Adding even more, thicker and larger overlying acquisition and dispersing layers did not at all resolve the above cited absorption, distribution and retention problems and moreover made the absorbent articles commercially unviable, environmentally unsustainable and more difficult to manufacture, store and transport.

Furthermore an existing problem which has been associated with such absorbent cores containing no or little cellulose fibers or fluff pulp is related to the migration, loss and leakage of the absorbent particulate polymer material from the absorbent article during dry and/or wet state, which leads to irritation, skin problems and overall discomfort for the user. This again is also especially true in the more homogenously distributed absorbent structures given their immobilization remains unsatisfactory to date. This lack of effective and efficient immobilization lead to dysfunctional absorbent articles due to lowered uptake capacity, gel blocking, enhanced rewet values, leakages and the creation of ruptures and/or pinholes through the liquid pervious topsheet and/or liquid impervious backsheet of such absorbent articles during manufacturing, high pressured packaging, transportation and storing, but also regular and prolonged usage by the user and/or caregiver.

Hence, there remains an urgent and clear need in the art for improved thin, flexible, lightweight absorbent articles comprising an absorbent structure that comprises an absorbent core comprising little to no fluff pulp or cellulose fibers that do not display the above problems and which are discreet, sustainable and/or relative inexpensive taking in mind manufacturing, marketing, design, fit, comfort, distribution, packaging, disposal, material, energy and transportation costs while preserving the required fluid absorption, distribution, transport, mechanical stability, coherence, thinness, rewet and retention properties and wherein the capacity, fit and comfort can be fully utilized. There is furthermore a need for a method and apparatus to produce such absorbent structures at high production speeds and low energy and raw material consumption.

The present invention aims to resolve at least some of the problems mentioned above.

The invention thereto aims to provide an absorbent article of which the absorbent structure comprises an absorbent core containing little to no fluff pulp or cellulose fibers and a high concentration of absorbent polymer material. The absorbent structure of the present invention is capable of overcoming the problems stated above by temporarily holding and subsequently releasing from the underlying release structure those fluids and liquids for subsequent absorption and permanent retention by the overlying absorbent core, and preferably by the absorbent polymer material therein. The present invention also relates to an absorbent article comprising such absorbent structure and to a method and apparatus for manufacturing such absorbent structure.

SUMMARY OF THE INVENTION

The present invention concerns an absorbent article comprising an absorbent structure. The absorbent article of the invention comprises a liquid pervious topsheet, a liquid impervious backsheet, and an absorbent structure positioned in between said backsheet and said topsheet, wherein the absorbent structure comprises an absorbent core positioned in between the topsheet and the backsheet, and a release structure positioned in fluid communication with the absorbent core, said absorbent core comprising little to no cellulose fibers or fluff pulp and said absorbent core comprising an absorbent polymer material for absorbing and permanently holding fluids received from the topsheet and the release structure, wherein said release structure comprises at least one non-woven fibrous substrate layer having the capacity to receive and temporarily hold the fluids in proximity to the absorbent core so that the fluids can subsequently be released to and absorbed by the absorbent core. The absorbent structure claimed herein solves at least some of the problems associated with essentially fluffless absorbent articles.

The release structure may be positioned between the absorbent core and the backsheet. Alternatively, or in addition, the release structure may be positioned between the absorbent core and the topsheet. Alternatively, or in addition, the release structure may be positioned within the absorbent core.

According to an embodiment of the invention the release structure comprises at least one layer.

According to an embodiment of the invention the release structure is in contact with the absorbent core.

According to an embodiment of the invention at least a part of the release structure is positioned between the absorbent core and the backsheet.

According to an embodiment of the invention at least a part of the release structure is positioned between the absorbent core and the topsheet.

According to an embodiment of the invention, the absorbent core has a topside facing the topsheet, a bottom side facing the backsheet and at least one side edge between the topside and bottom side, wherein at least part of the release structure is positioned along at least a portion of at least one side edge of the absorbent core.

According to an embodiment of the invention at least a part of the release structure is positioned within the absorbent core.

According to an embodiment of the invention the release structure is wrapped around the absorbent core.

The absorbent structure according to the present invention increases the instantaneous water holding capacity (IWHC), also denoted as instantaneous water holding capacity, and thereby improves the overall performance of the absorbent material contained therein and is capable of increasing the absorption, distribution, retention, transportation, redirection and/or redistribution of the bodily fluids and liquids within the absorbent article so as to more optimally utilize the function and structure thereof. For instance also the inability to fully absorb and retain liquids rapidly and completely when relatively large amounts of liquids are discharged into the absorbent article are resolved by an absorbent structure according to the invention. Also the inability of the absorbent: article to distribute, transport, redirect and/or redistribute from the saturated insult area towards the more distal unsaturated non-insult areas are hereby resolved. An absorbent structure according to the invention ensures a better controlled saturation of the absorbent component of the absorbent article which avoids excessive saturation, bulkiness and sagging of the wet, heavy absorbent material resulting into bad performance, limited product fit and poor wearing comfort.

The absorbent structure comprises at least one absorbent core containing little or no cellulose fibers or fluff pulp, such as a non-woven fibrous substrate layer having a void volume suitable to gather, contain and/or immobolize absorbent polymer materials, preferably absorbent particulate polymer materials, and at least one release structure below said absorbent core, i.e. to be placed between the absorbent core and the backsheet of the absorbent article. The release structure has a higher relative absorption capacity and/or absorption rate to temporarily hold and gradually release liquids in comparison with the upper absorbent core containing little or no cellulose fibers or fluff pulp. Note that as the absorbent core is positioned between top sheet and release structure, and the release structure is positioned between absorbent core and back sheet, the present document may refer to the absorbent core as an "upper" absorbent core or as being "above" the release structure. Vice versa, the present document may refer to the release structure as a "lower" release structure or as being "below" the absorbent core.

While the absorbent structure according to the invention comprises an absorbent core comprising absorbent polymer material having a more permanent liquid holding capacity, the release structure according to the absorbent structure as claimed in present invention has a more temporary liquid holding capacity. The inventor has found that the prior art absorbent articles comprising absorbent cores containing little or no cellulose fibers or fluff pulp in combination with the traditional higher mounted acquisition and/or dispersion layers (ADLs), i.e. ADLs positioned in between top sheet and absorbent core, are totally inadequate to absorb, distribute and retain fluids and liquids within said absorbent core due to the lack of cellulose fibers or fluff fibers and/or the inherent slow uptake capacity of the absorbent particulate polymer materials contained within such absorbent cores. Basically, the present inventor has found that in absorbent articles of the prior art, liquid insults penetrating the top sheet, can flow through the ADL and through the substantially fluffless absorbent core without being absorbed by either. Where the cellulose fibers or fluff fibers within traditional cellulose or fluff fiber containing absorbent cores were able to temporarily hold the fluids and prevent liquids from leaking outside of the absorbent structure until they were eventually taken up by the absorbent polymer materials contained within the absorbent core, such functional and structural liquid buffer is absent within the existing thin, flexible, lightweight absorbent articles comprising an absorbent core that comprises little to no fluff pulp or cellulose fibers. Many attempts have been undertaken to develop substantially cellulose free and/or essentially fluff pulp absorbent cores with classic overlying acquisition, dispersion and/or curly fiber layer to allow the underlying absorbent core to subsequently take up the fluids and liquids, however none of them seemed to have been able to solve the problems of the prior art described above.

Hence the inventors have developed an absorbent structure comprising an upper absorbent core containing little or no cellulose fibers or fluff pulp which is able to quickly let fluid and liquid pass in the z-direction towards the lower release structure which is able to temporarily hold and subsequently release fluid and liquid for absorption and permanent retention by the absorbent polymer material within the superimposed absorbent core. The present invention thus relates to an absorbent structure comprising an absorbent core and a release structure, as well as to an absorbent article comprising such absorbent structure and to a method and apparatus for manufacturing such absorbent structure and/or article.

The absorbent structure according to the present invention comprises an absorbent core which contains little or no cellulose fibers or fluff pulp. In an embodiment, the absorbent core comprises a nonwoven fabric layer with the absorbent polymer material contained, adhered and/or immobilized therein. The absorbent core can be in the form of a single core layer, or it can be of a multi-layer construction. For example, the absorbent core may include a first absorbent core layer of a first size, and at least one additional absorbent core layer overlying or underlying the first absorbent core layer and being of a different size and/or structural or functional properties than the first absorbent core layer. Multiple alternative compositions of absorbent core layers are possible to contain, adhere and/or immobilize absorbent polymer materials therein.

The absorbent core of the absorbent structure according to the present invention is positioned between the topsheet and the release structure to allow the fluids and liquids to quickly pass through the absorbent core towards the release structure, which helps to avoid that fluids and liquids from the first, second, third or further insults are blocked from being absorbed, distributed and/or retained by the absorbent core due to gel blocking, which could be leading to lowered uptake capacity, further gel blocking, enhanced rewet values, leakages and possibly the creation of ruptures and/or pinholes. Due to the fact that the more permanent liquid holding capacity shown by the absorbent polymer materials from the absorbent core is triggered and/or activated slower than the time it takes for the insults of fluid and liquid to pass through these thin, flexible and lightweight absorbent cores in the Z-direction towards the release structure the typical absorbent core containing little or no cellulose fibers or fluff pulp is unable to timely absorb and retain those fluids and liquids.

Preferably the article of the present invention is selected from the group consisting of a diaper, a light and/or heavy incontinent pad, a feminine care sanitary napkin and panty liner or a wound dressing.

Hence the absorbent structure in accordance with present invention comprises a release structure which functions as a underlying temporary holding capacity to immediately receive first, second, third and more insults and temporarily hold those fluids and liquids below the absorbent core containing little or no cellulose fibers or fluff pulp for a sufficient time until the fluid and liquid are subsequently and gradually absorbed by the absorbent polymer material in the superimposed absorbent core. So while the traditional cellulose fiber or fluff pulp containing absorbent structures and dysfunctional absorbent structure comprising absorbent core containing little or no cellulose fibers or fluff pulp from the prior art with acquisition and dispersion layers which are designed, positioned and superimposed towards the absorbent core to immediately acquire and disperse the fluids and liquids before they have even reached and/or entered the absorbent core lying underneath, the inventors found that this prior art approach does not work to obtain functional absorbent cores containing little or no cellulose fibers or fluff pulp. Hence they designed the absorbent structure according to the invention.

The release structure of the absorbent structure according to the present invention is positioned between the absorbent core and the backsheet to swiftly take up, temporarily hold and gradually release the fluid and liquids to the absorbent core in an upwards direction. The fluids and liquids released by the release structure may already have gone through the absorbent core in a downwards direction upon the respective first, second, third or following insult by the user but was not immediately, adequately and/or completely absorbed and/or retained by the superimposed absorbent core due to the very different absorption, distribution and retention properties of absorbent cores containing little to no cellulose fibers or fluff pulp and high relative amounts of absorbent polymer material.

In an embodiment, the release structure may be attached to the absorbent core, or it may be incorporated into the absorbent core where it may serve as the back layer and/or top layer of the absorbent core. In another embodiment, the release structure is separate from, but positioned in face-to-face relationship with a backside and/or topside of the absorbent core. Preferably, the release structure comprises a porosity, a wettability and a balance between the porosity and wettability, which allows it to immediately take up fluid coming through the absorbent core, temporarily hold it in close proximity to the absorbent core and subsequently release the fluid to the backside of the absorbent core, e.g. in an upwards direction, for absorption and retention by the absorbent polymer materials contained within said absorbent core.

The release structure is selected or designed for quickly receiving fluid insults in the downwards z-direction, holding them and gradually distributing them over a larger area of the release structure in the x-y dimension and subsequently releasing them again in the upwards z-direction and/or downwards z-direction.

In an embodiment the release structure suitably comprises a web, matt or bat of fibers or filaments, more preferably the release structure comprises a nonwoven fabric, more preferably an airlaid, drylaid, spunlaid, spunlaced, meltblown and/or carded nonwoven. Preferably hydrophilic, containing little to no absorbent polymer materials. In an embodiment the release comprises cellulose, wood pulp, fluff, curly fibers and/or other fibers suitable to obtain the desired relative absorption, absorption capacity and/or absorption rate. In an embodiment the release structure comprises absorbent materials including cellulose wadding; melt blown polymers; chemically stiffened, modified or crosslinked cellulosic fibers; tissue, including tissue wraps and tissue laminates; absorbent foams; absorbent sponges; absorbent polymer materials; absorbent gelling materials.

Examples of such suitable release structures are for instance cellulose-based structures with high instantaneous water holding capacity such as a highly absorbent airlaid of 50-150 grams, a viscose spunlaced material of 50-155 grams and/or 45/55 Viscose/PET layer of 100-135 grams. Paper-like materials such as tissues, wetlaid cellulose containing structures and/or laminates are also suitable.

Instantaneous water holding capacity (IWHC) of a release structure, absorbent core, absorbent structure and/or absorbent article can be measured with a IWHC testing procedure, which is a variation on the nonwoven standard procedure for measuring run-off (NWSP 080.9R0(15)). A static IWHC testing procedure and a dynamic IWHC testing procedure can be carried out to obtain values of a corresponding static IWHC of a test sample and a corresponding dynamic IWHC of a test sample, respectively. Both the static and dynamic IWHC testing procedure will be described in more detail in a later section of this application. Moreover, results obtained by carrying out the static and/or dynamic IWHC testing procedure on a variety of test samples will be shown and discussed.

In an embodiment according to the present invention, the absorbent structure comprises an absorbent core, which absorbent core comprises at least one substantially cellulose free and/or essentially fluffless fibrous substrate layer in which absorbent polymer material is dispersed and/or embedded. The substrate layer hereby aids in immobilizing the absorbent particulate polymer material and preferably also helps in distributing liquid across the absorbent structure, further contributing to an optimal use of the functional and structural capacities thereof. In one particular embodiment, the absorbent structure includes a carrier layer oriented toward the backsheet and an auxiliary layer oriented toward the topsheet, and wherein the absorbent structure is trapped between said auxiliary and carrier layers. While the absorbent core comprises absorbent polymer material, the release structure preferably does not comprise any absorbent polymer material. Given the absorbent polymer material can typically only absorb and retain fluids and liquids after having been exposed for a long enough time, these absorbent polymer materials would not be beneficial within the release structure given the release structures' main function is to temporarily hold the fluids and liquids until they are subsequently transferred and taken up again by the overlying absorbent core layer which does have relative high amounts of absorbent polymer materials showing permanent absorbency and retention characteristics. Obviously the release structure can contain little to small amount of absorbent polymer materials, but should preferably be considered substantially absorbent polymer material free. Bigger differential concentration of absorbent polymer materials in between absorbent core and the lack thereof in the release structure is beneficial.

Preferably the absorbent core and release structure surface area are of an equal size. The absorbent core and release structure may however also differ by more than about 75%, however preferably by only about 50%, even more preferably by only about 30% and most preferably by no more than about 5-20% from one another. This to ensure good fluid and liquid communication between them.

In an embodiment according to the present invention, the absorbent structure also comprises a substantially liquid impermeable and/or substantially absorbent particulate polymer material impermeable wicking layer which faces the backsheet of the absorbent article and/or side of the absorbent structure and extends along at least a part of the length, width and thickness of the absorbent structure, which further contributes to the prevention of dysfunctional absorbent articles and to the transporting, redirecting and/or distributing of liquids within the absorbent structure. Examples of such impermeable wicking layer are disclosed in co-pending patent application EP2992864A1 hereby incorporated by reference. The substantially liquid impermeable and/or substantially absorbent particulate polymer material impermeable wicking layer is hereby positioned below the release structure, i.e. on the other side of the release structure than the absorbent core and/or between the release structure and the backsheet of the absorbent article.

DESCRIPTION OF FIGURES

FIG. 3 shows an embodiment of the absorbent structure of the present invention, comprising an absorbent core and a release structure, but no acquisition layer and no dispersion layer.

FIG. 4 shows an embodiment of the absorbent structure of the present invention, comprising an absorbent core, a release structure and a dispersion layer above the absorbent core.

FIG. 5 shows an embodiment of the absorbent structure of the present invention, comprising an absorbent core, a release structure and an acquisition layer above the absorbent core.

FIG. 6 shows an embodiment of the absorbent structure of the present invention, comprising an absorbent core, a release structure and an acquisition and dispersion layer above the absorbent core.

FIG. 7 shows an embodiment of the absorbent structure of the present invention, comprising an absorbent core, a release structure and an upper nonwoven core wrap, but no acquisition layer and no dispersion layer.

FIG. 8 shows an embodiment of the absorbent structure of the present invention, comprising an absorbent core, a release structure and a lower nonwoven core wrap between absorbent core and release structure, but no acquisition layer and no dispersion layer.

FIG. 9 shows an embodiment of the absorbent structure of the present invention, comprising an absorbent core, a release structure, an upper core wrap above the absorbent core and lower core wrap in between the absorbent core and the release structure, but no acquisition layer and no dispersion layer.

FIG. 10 shows an embodiment of the absorbent structure of the present invention, comprising an absorbent core, a release structure and a lower nonwoven structure wrap below the release structure, but no acquisition layer and no dispersion layer.

FIG. 11 shows an embodiment of the absorbent structure of the present invention, comprising an absorbent core, a release structure, an upper structure wrap above the absorbent core and a lower structure wrap below the release structure, but no acquisition layer and no dispersion layer.

FIG. 12 shows an embodiment of the absorbent structure of the present invention, comprising an absorbent core, a release structure, an upper core wrap or an upper structure wrap above the absorbent core, an intermediate structure wrap or a lower core wrap in between the absorbent core and the release structure and a lower structure wrap below the release structure, but no acquisition layer and no dispersion layer.

FIG. 13 shows an embodiment of the absorbent structure of the present invention, comprising, an absorbent core, a release structure, an upper structure wrap above the absorbent core and a and lower structure wrap below the release structure, an acquisition and dispersion layer above the upper structure wrap.

FIG. 14 shows an embodiment of the absorbent structure of the present invention, comprising an absorbent core, a release structure and an edge barrier below and to the sides of the release structure and absorbent core, but no acquisition layer and no dispersion layer.

FIG. 15 shows an embodiment of the absorbent structure of the present invention, comprising an absorbent core, a release structure, an upper core wrap above the absorbent core and an edge barrier below and to the sides of the release structure, the absorbent core and the upper core wrap.

FIG. 16 shows an embodiment of the absorbent structure of the present invention, comprising an absorbent core, a release structure, an upper core wrap above the absorbent core, a lower core wrap in between the absorbent core and the release structure, and an edge barrier below and to the sides of the release structure, the absorbent core and the lower and upper core wrap.

FIG. 17 shows an embodiment of the absorbent structure of the present invention, comprising an absorbent core, a release structure, an upper structure wrap above the absorbent core, a lower structure wrap below the release structure, and an edge barrier below and to the sides of the release structure, the absorbent core and the lower and upper structure wrap.

FIG. 18 shows an embodiment of the absorbent structure of the present invention, comprising an absorbent core, a release structure, an acquisition and dispersion layer above the absorbent core and an edge barrier below and to the sides of the release structure, the absorbent core and the acquisition and dispersion layer.

FIG. 19 shows an embodiment of the absorbent structure of the present invention, comprising an absorbent core, a release structure, an acquisition and dispersion layer above the absorbent core, an upper structure wrap above the acquisition and dispersion layer and an edge barrier below and to the sides of the release structure, the absorbent core, the acquisition and dispersion layer and the upper structure wrap.

FIG. 20 shows an embodiment of the absorbent structure of the present invention, comprising an absorbent core, a release structure, an acquisition and dispersion layer above the absorbent core, an upper structure wrap above the acquisition and dispersion layer, a lower structure wrap below the release structure and an edge barrier below and to the sides of the lower structure wrap, release structure, the absorbent core, the acquisition and dispersion layer and the upper structure wrap.

FIG. 21 shows an embodiment of the absorbent structure of the present invention, comprising an absorbent core, a release structure, an acquisition layer above the upper structure wrap and an edge barrier below and to the sides of the release structure, the absorbent core, the upper structure wrap and the acquisition layer.

FIG. 22 shows an embodiment of the absorbent structure of the present invention, comprising an absorbent core, a release structure, a dispersion layer above the upper structure wrap, a lower structure wrap and an edge barrier below and to the sides of the release structure, the absorbent core, the upper and lower structure wrap and the dispersion layer.

FIG. 23 shows an embodiment of the absorbent structure of the present invention, comprising an absorbent core, a release structure, an acquisition and dispersion layer above the upper structure wrap, a lower structure wrap and an edge barrier below and to the sides of the release structure, the absorbent core, the upper and lower structure wrap and the acquisition and dispersion layer.

FIG. 26 illustrates an embodiment wherein the release structure is positioned centrally below the absorbent core.

FIG. 27 illustrates an embodiment wherein the release structure comprises multiple strips which are positioned below the absorbent core.

FIG. 28 illustrates an embodiment wherein the release structure is positioned below the absorbent core and along the side edges of the absorbent core, and extends along at least a part of the thickness of the absorbent core.

FIG. 29 illustrates an embodiment wherein the release structure is positioned below the absorbent core and along the side edges of the absorbent core, extends along the thickness of the absorbent core and is positioned at least partially above the absorbent core.

FIG. 30 illustrates an embodiment wherein the release structure is wrapped around the absorbent core.

FIG. 31 illustrates an alternative embodiment wherein the release structure is wrapped around the absorbent core.

FIGS. 37 to 50 are graphs which illustrate IWHC test results of various test samples. More in particular:

FIG. 37 illustrates static IWHC test results of a core wrap 8 gsm test sample.

FIG. 38 illustrates static IWHC test results of a spunlace 125 gsm test sample.

FIG. 39 illustrates static IWHC test results of a highloft 60 gsm test sample.

FIG. 40 illustrates static IWHC test results of an airlaid 55 gsm test sample.

FIG. 41 illustrates static IWHC test results of an airlaid 60 gsm test sample.

FIG. 42 illustrates dynamic IWHC test results of a core wrap 8 gsm test sample.

FIG. 43 illustrates dynamic IWHC test results of a spunlace 125 gsm test sample.

FIG. 44 illustrates dynamic IWHC test results of a highloft 60 gsm test sample.

FIG. 45 illustrates dynamic IWHC test results of an airlaid 55 gsm test sample,

FIG. 46 illustrates dynamic IWHC test results of an airlaid 60 gsm test sample.

FIG. 50 is a graph demonstrating tested values of IWHCd and IWHCs % parameters for core wrap 8 gsm, spunlace 125 gym, highloft 60 gsm and airlaid 55 gsm.

DETAILED DESCRIPTION OF THE INVENTION

Figure 1:
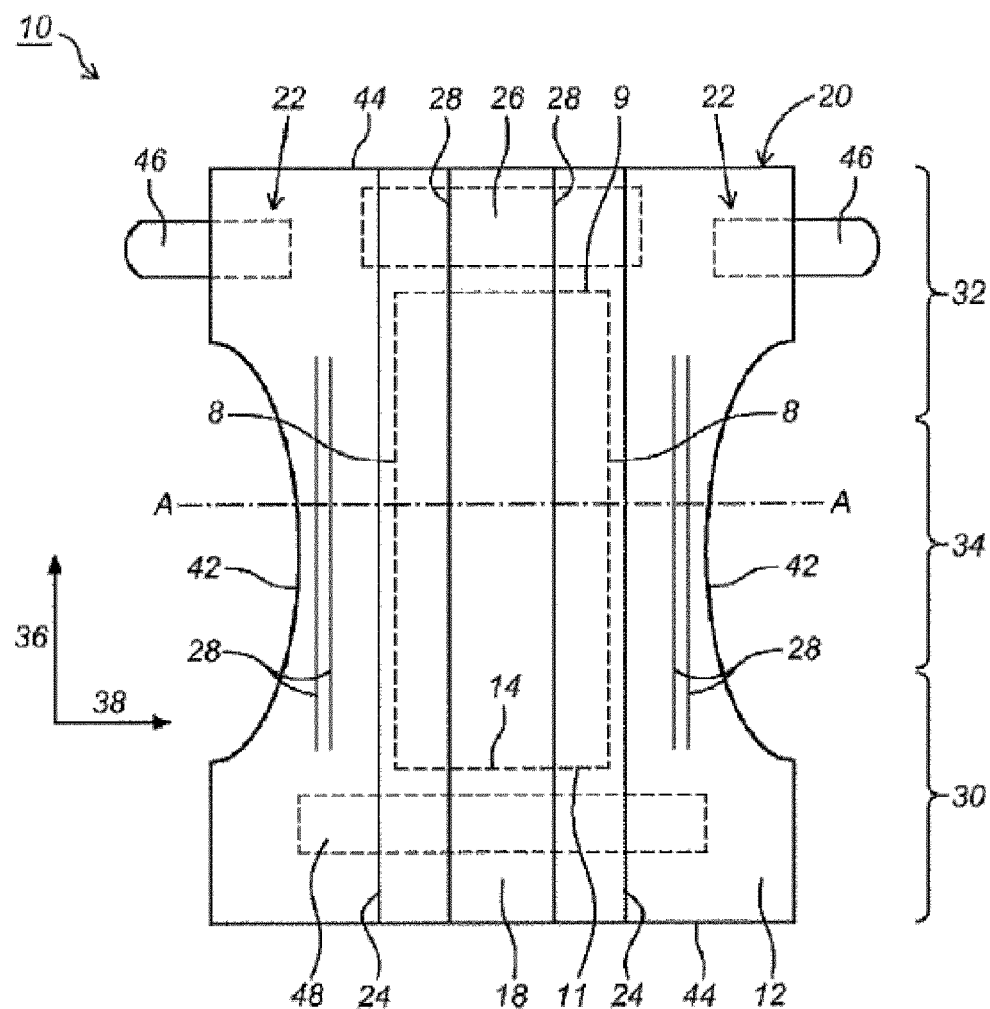
FIG. 1 is a top plan view of a diaper as a preferred embodiment of an absorbent article according to the present invention.

The present invention concerns an absorbent structure which comprises an substantially cellulose free and/or essentially fluffless overlying absorbent core and an underlying release structure, thereby reducing, the above functional and structural problems associated with the absorbent articles and allowing the absorption, distribution and/or retention capacity of the absorbent structure to be more optimally used. The absorbent structure may comprise one or more absorbent layers, components, elements and/or inserts, wherein the absorbent core and/or release structure may comprise one or more absorbent polymer materials and/or areas, such as for instance absorbent particulate and/or fibrous polymer materials, displaying relevant absorbency, absorption (rates) and/or adsorption (rates), capillary action, mass flow and so. Next to the absorbent core layer and the release structure the absorbent structure may comprise additional coverstock, acquisition layers and/or dispersion layers, which layer(s) may or may not be attached to one another, the chassis and/or the absorbent article by mechanical, thermal, physical, chemical, thermo-mechanical and/or ultrasonic bond strength and cohesion. The absorbent structure comprises an absorbent core fibrous substrate layer which is essentially cellulose free and/or essentially fluffless and contains absorbent polymer material, the release structure may comprise a web, matt, bat, nonwoven, woven, paper, tissue, knitted, tufted, stich-bonded, felted, films, airlaid, dry laid, wetlaid, spunlaid, spunlaced, meltblown, carded, staple, cellulose, wood pulp, fluff, curly fibers, fabrics, fibers, fabrics suitable to obtain desired structural and functional properties in accordance with the invention. Examples of suitable absorbent materials include creped cellulose wadding; melt blown polymers; chemically stiffened, modified or cross-linked cellulosic fibers; tissue, including tissue wraps and tissue laminates; absorbent foams; absorbent sponges; absorbent polymer materials; absorbent gelling materials; or any other known absorbent materials or combinations of materials. The use of cellulose fibers and/or fluff pulp is encompassed. The absorbent structure may further comprise minor amounts of non-liquid absorbent materials, such as adhesives, binders, plastics, waxes, oils and the like.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "an edge barrier" refers to one or more than one edge barrier.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment", "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to permanently absorb and/or retain bodily exudates.

"Absorbent component" as used herein refers to a structural constituent of an absorbent article, e.g., a piece of an absorbent core, such as one of multiple pieces in a multi-piece absorbent core.

"Absorbent element" as used herein refers to a part of a functional constituent of an absorbent structure, e.g., a acquisition layer, a dispersion layer, core layer or a release structure formed of a material or materials having particular liquid handling characteristics suitable for the specific function.

"Absorbent fibrous polymer material" as used herein refers to an absorbent polymer material which is in thread-like from such as fibers, filaments, and the like so as to be less flowable in the dry state than particulates.

"Absorbent insert" as used herein refers to a device adapted for insertion into an "Absorbent layer" as used herein refers to a term referring to a discrete, identifiable sheet-like or web-like element of an absorbent article which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g bond area's) or unintentional (e.g. manufacturing artifacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Absorption rate" as used herein refers to the rate of absorption of liquid, i.e. the amount of liquid which is absorbed per unit of time, typically by an absorbent component, element and/or absorbent layer of the absorbent article, structure and/or core.

"Acquisition layer", "acquisition region", "acquisition surface" or "acquisition material" and the like as used herein refer to the layer overlying the absorbent core having a faster liquid uptake and/or distribution capability.

"Absorbency" is the ability of a material to take up fluids by various means including capillary, osmotic, solvent, chemical and/or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibers or particles in an air stream and condensing them from the air stream onto a moving screen by means of a pressure and/or vacuum; a web of fibers produced by airlaying is herein referred to an "airlaid"; an airlaid web bonded by one or more techniques to provide fabric integrity is herein referred to an "airlaid nonwoven".

"Apparent density", "density" as used herein refers to the basis weight of the sample divided by the caliper with appropriate unit conversions incorporated therein. Apparent density used herein has the unit $g/cm^3$.

"Attach", "attached" and "attachment" as used herein are synonymous with their counterparts of the terms "fasten", "affix", "secure", "glue", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, $g/m^2$ or gsm.

"Bodily exudates", "body exudates", "bodily fluids", "body fluids", "bodily discharges", "body discharges", "fluid(s)", "liquid(s)", "fluid(s) and liquid(s) and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fiber) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibers" as used herein refers to naturally occurring fibers based on cellulose, such as, for example cotton, linen, etc; wood pulp fibers are one example of cellulose fibers; man-made fibers derived from cellulose, such as regenerated cellulose (rayon), or partially or fully acetylated cellulose derivatives (e.g. cellulose acetate or triacetate) are also considered as cellulose fibers.

"Cluster" or the like as used herein refers to an agglomeration of particles and/or fibers.

"Chemically stiffened fibers", chemically modified fibers", "chemically cross-linked fibers", "curly fibers" and the like as used herein are used interchangeably and refer to any fibers which have been stiffened by chemical means to increase stiffness of the fibers under both dry and aqueous conditions, for example by way of addition of chemical stiffening agents (e.g. by coating, impregnating, etc), altering the chemical structure of the fibers themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight nonwoven material used to contain and conceal an underlying absorbent core material; examples are the facing layer or materials that cover the absorbent cores of feminine hygiene garments, baby diapers and pants and adult incontinence garments.

"Crotch region" of an absorbent article as used herein refers to about 50% of the absorbent article's total length (i.e., in they-dimension), where the crotch point is located in the longitudinal center of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them in soluble.

"Diaper", "conventional diaper", "diaper-like", "diaper-like garment" and the like as used herein are used interchangeably and refer to disposable absorbent articles, which typically include a front waist portion and a back waist portion which may be releasable connected about the hips of the wearer during use by conventional fasteners such as adhesive tape fasteners or hook and loop type fasteners. In use, the article is positioned between the legs of the wearer and the fasteners are releasable attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Dispersion layer", "dispersion region", "dispersion surface" or "dispersion material" and the like as used herein refer to the layer overlying the absorbent core having a faster liquid uptake and dispersion capability.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Drylaying" as used herein refers to a process for making a nonwoven web from dry fiber; these terms apply to the formation of carded webs, as well as to the air laying formation of random webs; a web of fibers produced by drylaying is herein referred to as a "drylaid"; a dry-laid web bonded by one or more techniques to provide fabric integrity is herein referred to a "drylaid nonwoven".

"Dry strength" as used herein refers to the strength of ajoint determined in dry state conditions, immediately after drying under specified conditions or after a period of conditioning in the standard laboratory atmosphere.

"Essentially cellulose free" or "little to no cellulose fibers" as used herein refers to an absorbent article, structure, core component and/or element containing less than 20% by weight cellulosic fibers, less than 10% cellulosic fibers, less than 5% cellulosic fibers, no cellulosic fibers, or no more than an immaterial amount of cellulosic fibers which do not materially affect the thinness, flexibility or absorbency thereof.

"Essentially fluffless" or "little to no fluff pulp" as used herein refers to an absorbent article, structure, core, component and/or element containing less than 20% by weight fluff pulp, less than 10% fluff pulp, less than 5% fluff pulp, no fluff pulp, or no more than an immaterial amount of fluff pulp which do not materially affect the thinness, flexibility or absorbency thereof.

"Fabric" as used herein refers to a sheet structure made from fibers, filaments and/or yarns.

"Feminine hygiene garments" as used herein refer to absorbent hygiene articles intended to be worn by woman, for absorbing and containing body exudates.

"Fiber" as used herein refers to the basic threadlike structure from which nonwovens, yarns and textiles are made. It differs from a particle by having a length at least 4 times its width; "Natural fibers" are either of animal (wool, silk), vegetable (cotton, flax, jute) or mineral (asbestos) origin, while "Man-made fibers" may be either polymers synthesized from chemical compounds (polyester, polypropylene, nylon, acrylic etc.) or modified natural polymers (rayon, acetate) or mineral (glass). "Fiber" and "filament" are used interchangeably.

"Fluff pulp" or "Pulp fluff" as used herein refers to wood pulp specially prepared to be drylaid. The fibers can be either natural or synthetic or a combination thereof.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the backsheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"High loft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilization layer" as used herein refers to a layer able to be applied to the absorbent polymer material or absorbent polymer material area with the intent to gather, bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibers with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and/or faces the wearer facing layer; conversely, the term "lower" refers to the layer of the absorbent article which is nearest to and/or faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the flow of a liquid from one absorbent element or component to another absorbent element or component by channel flow action.

"Mechanical bonding" as used herein refers to a method of bonding fibers by entangling them. This can be achieved by needling, stitching with fibers or by the use of high-pressure air or water jets and the like.

"Nonwoven" as used herein refers to manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm). "Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or nonrefastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Release structure", "release region", "release surface" or "release material" and the like as used herein are used interchangeably and refer to a structure in fluid communication with the absorbent core having a larger relative liquid absorption capacity and/or rate allowing it to quickly take up, temporarily hold and releasing liquids.

"Resin" as used herein refers to a solid or semisolid polymeric material.

"Thermobonding" as used herein refers to a method of bonding fibers by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localized heat through vibration thereby causing thermoplastic fibers to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibers produced by weaving is herein referred to as a "woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (they-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or nonwoven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibers by applying modified paper making techniques; a web of fibers produced by wetlaying is herein referred to as a "wetlaid".

"Wood pulp" as used herein refers to cellulosic fibers used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

The recitation of numerical ranges by endpoints includes all numbers and fractions subsumed within that range, as well as the recited endpoints.

In a first aspect, the current invention provides an absorbent article comprising a liquid pervious topsheet, a liquid impervious backsheet, and an absorbent structure positioned in between said backsheet and said topsheet. The absorbent structure comprises an upper absorbent core and a lower release structure.

In a preferred embodiment of the present invention, the absorbent structure comprises an absorbent core as disclosed in patent documents WO 2013/153235 A1 or WO 2013/152809 A1, which are hereby incorporated by reference.

The inventors have developed an absorbent structure comprising a superimposed absorbent core containing little or no cellulose fibers or fluff pulp in combination with an underlying release structure. Said absorbent core preferably comprises absorbent polymer materials having a homogenous and/or heterogeneous distribution and a fibrous nonwoven hydrophilic or hydrophobic substrate layer. The absorbent structure and/or the absorbent core is in a preferred embodiment covered by core wrap layer such as a spunbond, PE film, PET film, polyolefin, multilayer films, coextruded films, carded nonwoven or any suitable material.

In a preferred embodiment of the invention, the absorbent structure comprises an absorbent core with from about 0.1 to 1000 gsm of absorbent polymer materials, a preferred quantity of absorbent particulate polymer material for baby diapers or adults incontinence ranges from 100 to 500 gsm and from 10 to 200 gsm in feminine care products. The release structure contains preferable from about 100-300 gsm, preferably between 10 to 300 gsm, more preferably 20 to 250 gsm, even more preferably between 25 and 250 gsm, even more preferably between 30 to 150 gsm, yet more preferably between 50 and 150 gsm, most preferably between 35 to 135 gsm, even most preferably between 70 and 135 gsm consisting of natural and/or synthetic fibers.

An absorbent structure according to the invention has a lateral dimension ranging from 0.1 to 800 mm. Depending on the different application, said absorbent structure typically has a lateral dimension of 50 to 180 mm for baby diaper products; from 30 to 250 mm for adult incontinence products and from 30 to 90 mm for feminine care products. An absorbent structure according to the invention preferably has an absorbent core comprising a maximum length of between 100 mm and 800 mm, more preferably between 150 mm and 650 mm, yet more preferably between 250 mm and 550 mm and a maximum width of between 30 mm and 500 mm, more preferably between 50 mm and 400 mm, still more preferably between 100 mm and 250 mm, and whereby the release structure is comprising a maximum length of between 100 mm and 800 mm, more preferably between 150 mm and 650 mm, yet more preferably between 250 mm and 550 mm and a maximum width of between 30 mm and 500 mm, more preferably between 50 mm and 400 mm, still more preferably between 100 mm and 250 mm.

An absorbent core containing little or no cellulose or fluff means the structure for absorbing and containing liquid received by the absorbent article and may comprise one or more substrates, absorbent polymer material disposed on the one or more layers above, in between and/or underneath the absorbent particulate polymer material for immobilizing the absorbent particulate polymer material on the at least one substrate.

The absorbent core in accordance with the absorbent structure of the invention is essentially cellulose free and/or fluffless. In certain embodiment, the absorbent core would consist essentially of at least one substrate, the absorbent polymer material, the immobilization layers and/or optionally the auxiliary, carrier and/or cover layer. The absorbent core substrate typically comprises a basis weight in the range of 3-500 gsm, more preferably 10-150 gsm, even more preferably 15-120 gsm, most preferably 20-100 gsm, whereby a variety of materials can be used. The absorbent substrate of the absorbent core is liquid permeable over at least part of its surface so that liquids can pass in the Z-direction towards and from the release structure. In an embodiment, the substrate of the absorbent core is provided, and preferably wrapped, with a lower and/or an upper wrap layer which are liquid permeable. In a preferred embodiment, the absorbent core includes a rear carrier layer oriented toward said backsheet, and an auxiliary layer of nonwoven fabric oriented toward said topsheet, and the absorbent polymer particles are trapped between said front and rear carrier layers. If two wrap layers are used to cover the absorbent core or absorbent structure, the edges of said layers are preferably attached to seal the structure. If one structure core wrap layer is used, said layer is folded to wrap the absorbent core and/or absorbent structure and the edges are preferably attached to seal the structure. These wrap layers may be folded in a G-, C- or otherwise in order to prevent the migration and/or loss of absorbent polymer materials. The sealing can be done by any bonding techniques known in the art.

An absorbent core according to the invention can be obtained by penetrating a nonwoven fibrous substrate with absorbent polymer materials know in the art, and may comprise up to 1000 gsm of absorbent polymer material, preferably about 200 to about 500 gsm of absorbent polymer, even more preferably about 250 to about 450 gsm of absorbent polymer materials depending on the body fluid holding capacity. The absorbent polymer material can be heterogeneously distributed throughout the absorbent core such as in compartment, clusters or islands of absorbent polymer materials, alternatively the absorbent polymer material can be homogeneously distributed such as a substantially evenly or uniformly spread absorbent polymer material area. The absorbent structure according to the invention encompasses both the heterogeneously as well as the homogeneously spread absorbent polymer material areas.

In a preferred embodiment of the invention, the absorbent core comprises absorbent particles having one particle size. In another, more preferred embodiment, the absorbent core comprises absorbent particles having more than one particle size, whereby preferably the absorbent particles are distributed in the absorbent core according to a gradient of the particle size in the x, y and/or z-direction. Preferably, the average particle size is distributed in the z-direction whereby the larger size absorbent polymer materials are localized in the lower side of the absorbent core, being preferably 250 to 800 micron, more preferably 325 to 450 micron, while the size of the absorbent polymer materials of the smaller size absorbent polymer materials localized at the upper side of the absorbent core, being preferably 75 to 350 micron, more preferably 110 to 275 micron.

When such an absorbent core according to a preferred embodiment of the invention is manufactured, absorbent particles of different sizes can be distributed on a substrate, whereby the smaller absorbent polymer materials penetrate more deeply into the lower part of substrate, along the z-direction, while larger absorbent polymer materials remain on the upper part of the substrate. Subsequently, the substrate provided with the absorbent particles can be used in an absorbent core in a turned-over state such that the particles of smaller size are positioned above, i.e. to the wearer-facing side of the absorbent core, while the particles of bigger size are positioned at the bottom, i.e. to the garment-facing side. Given that smaller absorbent polymer materials are sufficiently distant from one another in between the fibers and filaments of the upper regions of the fibrous substrate of the absorbent core, gel blocking can be prevented or at least decreased in an absorbent structure according to the present invention.

Liquid insults coming from the top sheet are hereby allowed to at least partially run and seep through the absorbent core, whereby the smaller particles at the top of the absorbent core are sufficiently distant from each other such that gel-blocking does not occur and whereby the larger absorbent particle near the bottom of the absorbent core do not have the time to take up all liquid that seeps through at the position of an insult, thereby ensuring that no gel-blocking occurs near the bottom of the absorbent layer. The part of the liquid that seeps through the absorbent core at the x-y position of the insult can still be substantial and is temporarily taken up by the release structure below the absorbent core which has a high absorption rate and has the capacity to disperse the liquid in the x-y direction towards regions of the absorbent core which has absorbent particles which have not yet been exposed or have been exposed only partially to the liquid. At these regions, the liquid which was temporarily stored in the release structure can be absorbed by the absorbent core, e.g. under the influence of wicking or of pressure gradients which are typically present during use of the absorbent article. Also, at these regions, no gel-blocking is present. Hence, the combination in this embodiment of an absorbent core with a gradient in particle size along the z-direction and a release structure seems to provide a clear advantage with respect to reducing gel-blocking. Note that the absorbent polymer materials can be dispersed in the fibrous substrate and are maintained in the fibrous substrate by entrapment or entanglement and/or after an optional binding step wherein absorbent polymer materials are bonded by the addition of glue.

According to an embodiment of the invention, the absorbent core comprises a non-woven fibrous substrate comprising a dual layer, an upper layer which has acquisition and dispersion functions for a fast liquid acquisition and a good distribution of the liquid over the surface of the lower layer. According to an another embodiment of the invention, the absorbent core comprises a non-woven fibrous substrate comprising a triple layer, an upper layer which has acquisition and dispersion functions for a fast liquid acquisition and good distribution of the liquid over of the liquid, an intermediate layer suitable to prevent the liquid to return to the surface thereby improving low rewet values and a lower layer, said fibrous lower layer may comprise absorbent polymer materials thereby forming an absorbent polymer material area beneath the intermediate layer. Preferably, the absorbent particle polymer materials are distributed in the absorbent core depending on a profile along at least one dimension of said absorbent structure. In a preferred embodiment, the absorbent particles are deposited depending on a profile along a x-direction of said absorbent structure. In a preferred embodiment, the absorbent particles are deposited depending on a profile along a y-direction of said absorbent structure. In a preferred embodiment, the absorbent particles are deposited depending on a profile along a z-direction of said absorbent structure. The intermediate layer is preferably very hydrophilic so that the liquid is able to spread over the core. Said intermediate layer is also non-porous, to prevent the fluid to return to the top surface and to maintain the absorbent polymer materials within the lower layer during application, but also during the use of the absorbent article, once the absorbent articles are swollen by liquid. The lower layer is a very porous structure suitable for being penetrated with absorbent particle polymer materials, said bottom layer serves as a permanent absorption layer. Multilayer absorbent cores also prevent the migration of the absorbent polymer materials from the absorbent core. Alternatively, at least one core wrap or structure wrap layer is used to prevent migration or loss of absorbent polymer materials from the absorbent core.

The absorbent structure according to the invention contains an absorbent core and a release structure, they can be unitary or separate components. The absorbent core and release structure can be bonded to one another using any means known in the art. The attachment can be done by using a nozzle system which can provide a relatively thin but wide curtain of adhesive. This glue curtain can be continuous or discontinuous, so as to be applied in a homogeneous or heterogeneous surface or can be applied in various combinations of lines, grids, spirals, figures, spots, dots, etc. either in a determined or undetermined location of the target surface and/or any combination thereof. The inventors have found that the heterogeneous surface binding in between the back of the absorbent core and the top of the release structure can be preferably done by lines, grids and most preferably spirals to accommodate the downward and upward flow of fluids and liquids from the absorbent core to the release structure and back. It has been found that compositions most useful are those which combine controlled cohesion and adhesion behavior. Adhesion is preferred to ensure that the layers maintain sufficient contact with one another. Cohesion ensures that the attachment does not unintentionally detach or keeps attached, in particular in response to external forces, and namely in response to strain. The attachments in between the layers are subject to external forces during usage and when the absorbent structure swells due to the acquired liquid.

The release structure is positioned underneath the absorbent core and is intended to temporarily acquire fluids and liquids that pass downwards through the absorbent core in the z-direction and to transport and distribute these fluids over a larger area of the release structure so that the full extent of the overlying absorbent core can subsequently be utilized for (re)absorbing the fluids and liquids in the upwards z-direction. The release structure according to the invention will prevent gel blocking in essentially cellulose free and/or fitness absorbent cores having relative high concentration of absorbent polymer materials. To provide the rapid temporary absorption, transport and distribution function, the release structure preferably has a relative open porous structure. The release structure may comprise a layered structure, preferably with same or differing fiber sizes and/or pore sizes.

The release structure according to the absorbent structure of the invention comprises at least one and preferably a plurality of layers of web, matt or bat of fibers or filaments, more preferably the release structure comprises a nonwoven, woven or other fabrics, more preferably laid via airlaid, drylaid, spunlaid, spunlaced, meltblown and/or carded, that have a capacity to receive the fluid insults from the absorbent core and to temporarily hold the fluid insults until the overlying absorbent core comprising relative high concentration of absorbent polymer material can absorb the fluids. Next to transportation and distributing of the fluids, the underlying release structure functions primarily to temporarily immobilize or hold the fluids in close proximity to the overlying absorbent core comprising relative high concentration of absorbent polymer material and subsequently release the fluids upwards into the absorbent core. This can be achieved through a balance of the pore size of the fabric and the wettability of the fibers.

Preferably, the webs, nonwovens and/or fabrics used in the release structure have a calculated average pore size of less than 200 μm, such as less than 100 μm, or as less than about 70 μm. Additionally, while in use, the release structure and the absorbent core are typically pressed against each other, which assists in releasing the fluids from the release structure to the absorbent core. Various kinds of materials can be used in producing compositions. Examples of suitable webs, nonwovens and fabrics include spunlaid, spunlace, carded or staple webs, carded thermal bond webs, spunbond webs, air laid, drylaid and wet laid webs. Particularly advantageous fluid handling and/or wetting properties can be achieved by using carded staple fiber webs that utilize fiber combinations of various sizes, polymer compositions and surface characteristics to improve the fluid penetration rate and short-term fluid retention of the temporary storage layer.

The release structure which is typically formed separately from the absorbent structure, is designed to receive and release fluid and liquid exuded by the wearer. The release structure preferably comprises hydrophilic fibers (e.g., cellulose, fluff and related fibers), which are loosely mixed and entangled together to form a web and/or bonded to the form a nonwoven. Thermoplastic polymer fibers may also be included to provide a reinforcing matrix. The release structure must be formed, bonded, shaped, and/or cut to form individual absorbent structure suitable for the particular absorbent articles. In an embodiment the release structure comprises cellulose, wood pulp, fluff, curly fibers and/or fibers suitable to obtain the desired absorption, absorption capacity and/or absorption rate. In an embodiment the release structure comprises absorbent materials including cellulose wadding; melt blown polymers; chemically stiffened, modified or cross-linked cellulosic fibers; tissue, including tissue wraps and tissue laminates; absorbent foams; absorbent sponges; absorbent polymer materials; absorbent gelling materials. Further examples of potential release structure material are cellulosic fibers, fluff pulp, cellulose-containing web structures, tissue layers, absorbent foam materials, absorbent nonwoven materials and the like. These materials are preferably hydrophilic, but can also be hydrophobic or a combination thereof.

In an embodiment, the release structure comprises a nonwoven fabric having an open porous structure and a calculated average pore size greater than 100 μm, and more typically from about 135 to 165 μm, and the nonwoven fabric of the release structure includes hydrophilic fibers or filaments. In a preferred embodiment, the release structure is a nonwoven fabric formed of fibers or filaments, wherein said at least one layer of nonwoven fabric in the release structure has fibers or filaments of a size smaller than the fibers or filaments of the absorbent core. In another preferred embodiment, the release structure is separate from, but positioned in face-to-face relationship with the back of the absorbent core. In a preferred embodiment, a structure wrap release structure is provided, preferably comprising an average pore size less than about 70 μm. In a preferred embodiment, the release structure comprises at least one layer of a spunlaced material of between 15-250 gsm base weight, more preferably between 50-150 gsm, most preferably between 70-135 gsm consisting of synthetic and/or natural fibers. In a preferred embodiment, natural fibers such as viscose, cotton, cellulose, fluff pulp or the like are being used. They compose from 0-100% of the release structure, preferably 25-100%, more preferably 50-100% and most preferably at least 85-90%. The fibers used in the release structure can be hydrophilic, hydrophobic and/or a combination of hydrophilic and hydrophobic fibers in order to provide the desired fluid absorption and release properties.

Preferably the relative liquid absorption capacity and/or rate of the release structure is higher than the relative absorption capacity and/or absorption rate of the absorbent core, thereby obtaining the desired fluid and liquid characteristics of the absorbent structure. The release structure is preferably very hydrophilic and/or more hydrophilic than the overlying absorbent core to enhance the fluid uptake and release in accordance with the invention. The release structure preferably having relatively more pores absorbs fluids faster than the absorbent core having relative fewer pores clue to the low amount or total lack of cellulose fibers or fluff pulp layers. The release structure preferably having smaller fiber denier than the relative fiber size of the absorbent core fibrous substrate thereby further accommodating faster fluid absorption, absorption capacity and/or absorption rate within the release structure in comparison to the absorbent core. According to a preferred embodiment of the absorbent structure according to the invention, the relative absorption, absorption capacity and/or absorption rate of the release structure comprising fibers such as preferably natural, cellulose and/or fluff fibers have typically higher water absorption, absorption capacity and/or absorption rates than the man-made, polyethylene, polypropylene and similar fibers, however the release structure can either use the natural, synthetic or man-made fibers and/or a combination thereof. In absorbent structures containing little to no cellulose and/or fluff fibers the absorption, absorption capacity and/or absorption rates are typically not sufficient to prevent leakage, malfunctioning and/or high rewet values. Therefore the inventors have found it extremely beneficial to combine different fibrous substrates into the absorbent structure to ensure beneficial absorption, distribution and retention rate of the resulting absorbent article. The relative difference in between pore, denier and/or fiber materials in between the absorbent core and the release structure may further beneficially influence the absorbency and/or capillary pressure which allows the fluids and liquids to move upwards from the release structure into the absorbent core along the z-direction. The fluid surface tension is important for the fluid-media contact angle and absorption wetting, capillary pressure is directly proportional to surface tension and the fluid-surface contact angle. Given that high fluid surface tension leads to high contact angles, the effect of high surface tension reduces fluid penetration, hence fibers showing lower surface tension have a higher fluid transportation. The fluid absorption and permeation into the fibrous porous media such as those of the absorbent core and release structures depend on the actual substrate characteristic and the interaction in between the fluids and those substrates. The absorbent structure absorption, absorption capacity and/or absorption rate is a combination due to the difference in relative pore volume, fiber dimensions and the surface chemistry and/or contact angle of the substrate is involved. How the fluid and liquids contact and wet the absorbent core and release structure effect both the volume and fiber absorption, therefore the relative relation in between the absorbent core and release structure can be developed so as to meet the requirement of the present invention. Typically the depth of the fluid and liquid penetration is proportional to the pore size of the substrate, which is also related to the absorption, absorption capacity and/or absorption rate. As the pore size increases, absorption volume decreases, which can also be seen in the absorbent core fibrous structures which due to little to no cellulose and/or fluff pulp lead to low absorption, absorption capacity and/or absorption rates and thus lead to the fact that the initial insults run and seep immediately through the absorbent core in de downwards z-direction. It is only a slower pace absorption through for instance the capillary action that subsequently allows the fluids and liquids to be gradually taken up again by the absorbent core overlying the release structure. Therefore it is preferred that the underlying release structure preferably has ideal pore radius values in comparison with the pore radius values of the fibrous substrate of the absorbent core and/or core wraps. Absorption, absorption capacity and/or absorption rate of fluid is found to be affected by the fibrous substrate surface chemistry and obviously also the fluid and liquid properties, whereby the contact angle is typically used to characterize the fiber surface chemistry. The low contact angles lead to high absorption, absorption capacity and/or absorption rate while the high contact angles lead to low absorption, absorption capacity and/or absorption rate. This in combination with relative pore and fibers sizes of the absorbent core and release fiber layer allows for manufacturing absorbent structures according to the present invention. The absorption, absorption capacity and/or absorption rate is also influenced by the penetration times, to help develop the required absorbent core and release structure fiber structures. The capillary pressure however remains one of the driving forces behind the take up and/or release by the release structure and absorption and reabsorption by the absorbent core. By structuring the characteristics of the fibers, pores and capillary pressure factors the inventors have found that the absorbent structure according to the invention shows beneficial absorption, distribution and retention. Especially in cellulose fibers and pulp fluff used in the release structure temporarily take up fluid and liquids, transports it to non-saturated areas of the release structure until the fibers and filaments of the release structure start to swell and subsequently slow down, prevent and block further absorption upon which the capillary pressure in between the absorbent core and the release structure and start to draw liquid from the release into the absorbent core. The swelling of the fibers can for instance block the pores and thereby prevent further absorption and also initiates the release process. The use of cellulose and/or fluff pulp fibers are especially advantageously due to their high liquid absorbency rate, wettability, pore size, fiber denier and/or size as well has the surface contact angle or surface chemistry have proven to be ideally to manufacture the release structure underlying the absorbent core showing little or no cellulose or fluff pulp fibers. Some of the objective criteria for the quality determination of cellulose fibers or fluff pulp are: high absorption capacity and low time of absorption, high specific volume wet, high bulk after wetting, compression and spring back, high rate of absorption, high strength and high brightness. The various ways of manufacture are based on additives of various chemicals which can work as a cross linking agent of the cellulose, i.e. to achieve chemical bonding between the cellulose molecules within the particular cellulose fibers, or the use of synthetic resins. Through the use of these fibers, which are stiffer in wet condition, there is achieved a body of fluff within the release structure giving increased absorption capacity and which moreover distributes the liquid throughout the whole volume of the release structure. These properties of the cellulose or fluff pulp within the release structure are of great significance in relation to the high amount of relative absorbent polymer materials in the absorbent core.

In one embodiment of the invention, the release structure is a separate individual component, and it is positioned underneath the absorbent core and below a lower wrap or carrier layer during the fabrication of the absorbent article. In another embodiment, the release structure can be bonded, such as via mechanical, thermal, physical, chemical, thermo-mechanical and/or ultrasonic, to the backside layer of the absorbent core so that these components can be handled as a unit during fabrication of the absorbent article. In yet another embodiment, the release structure can be incorporated into the structure of the absorbent core as part of its lowermost carrier layer.

The absorbent core and/or the absorbent structure is preferably wrapped between two layers of nonwoven. The lower nonwoven of an absorbent structure wrap is preferably attached to the bottom surface of the release structure. The upper nonwoven is preferably attached to the top surface of the absorbent core. In a preferred embodiment, the widths of the core wrap nonwovens exceed the width of absorbent structure, so that the nonwovens can be bonded with each other along the side edges. In a preferred embodiment, such nonwoven is at least partially and preferably completely folded around the absorbent structure and sealed on top or bottom. In a preferred embodiment, a cupshape configuration is provided whereby the side edges of the lower core wrap are folded on top of the core. In an alternative embodiment, no core wrap is provided.

In an embodiment according to the invention, the absorbent structure comprises an absorbent core, a release structure and an edge barrier between the release structure and the backsheet, preferably at least partially following side edges of the absorbent structure. The edge barrier preferably extends along the entire thickness of the absorbent structure, the absorbent core and/or release structure of the absorbent structure, where it extends along at least a part of the length and/or width of the absorbent structure, preferably wherein the edge barrier comprises a hydrostatic head of at least 100 mm.

In an embodiment, the edge barrier is folded double along the x-axis and/or y-axis. In a preferred embodiment, the edge barrier is disposed along at least a part of both side edges. In a preferred embodiment, the edge barrier is disposed along at least a part of both side edges, the front edge and/or the back edge.

In an embodiment, the absorbent structure comprises a substantially liquid impermeable and/or substantially absorbent particulate polymer material impermeable wicking layer, which wicking layer faces the backsheet of the absorbent article and extends along at least a part of the length and width of the absorbent structure, preferably wherein the wicking layer comprises a hydrostatic head of at least 100 mm. In an embodiment, the wicking layer and the edge barrier are made out of one single piece of material, preferably said single piece of material comprising a substantially continuous layer of foil, film, closed foam, plastic and/or nonwoven material.

A method to prepare an absorbent structure suitable for the invention comprises the steps of: unwinding a fibrous substrate, covering the substrate with the absorbent polymer material, e.g. by powder scattering or by drum formation, through vacuum technology of a standard diaper line and/or preferably applying an alternative electrical field to ensure a homogeneous distribution of the SAP particles, this method is also known as the Fibroline method described in EP1526214 or EP 2165015 each incorporated herein by reference. An absorbent structure according to the present invention can be manufactured by providing the absorbent core with a release structure. The absorbent core is preferably bonded to the release structure using one of the following non-limitative bonding methods such as powder coating and thermo bonding, heat treatment, spray coating, powder scattering, reactive glue (activation and curing) or any combination thereof.

The present invention also concerns a device suitable to perform the methods disclosed here above, wherein preferably the device is in line or off line of absorbent core and release structure absorbent structure production line for an absorbent article.

FIG. 1 is a top plan view of a diaper 10 as a preferred embodiment of an absorbent article including an absorbent structure 14 according to the present invention. It should be understood, however, that the present invention is also applicable to other absorbent articles such as feminine hygiene garments, baby pants, adult incontinent garments and the like.

The absorbent article is shown in its flat out, un-contracted state with the wearer side facing the viewer. The chassis 12 of the diaper 10 in FIG. 1 comprises the main body of the diaper 10. The chassis 12 comprises an outer covering including a liquid pervious topsheet 18 and/or a liquid impervious backsheet 20. The chassis 12 may include a portion of an essentially fluffless absorbent structure 14 encased between the topsheet 18 and the backsheet 20. The chassis 12 may also include most or all of the absorbent structure 14 encased between the topsheet 18 and the backsheet 20. The chassis 12 preferably further includes side panels or ears 22, elasticized leg cuffs 28 and elastic waist features 26. One end portion of the diaper 10 is configured as a front waist region 30 of the diaper 10. The opposite end portion is configured as a back waist region 32 of the diaper 10. An intermediate portion of the diaper 10 is configured as a crotch region 34, which extends longitudinally between the first and second waist regions 30 and 32. The waist regions 30 and 32 may include elastic elements such that they gather about the waist of the wearer to provide improved fit and containment (e.g. elastic waist feature 26). The crotch region 34 is that portion of the diaper 10 which, when the diaper 10 is worn, is generally positioned between the wearer's legs. The diaper 10 is depicted with its longitudinal axis 36 and its transverse axis 38. The periphery of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper. The chassis 12 also comprises a fastening system, which may include at least one fastening or securing member 46 and at least one landing zone 48. The various components within the diaper 10 may be bound, joined or secured by any method known in the art, for example by adhesives in uniform continuous layers, patterned layers or arrays of separate lines, spirals or spots. The topsheet 18, the backsheet 20, the absorbent structure 14 and other components may be assembled in a variety of well-known configurations and are well known in the art.

The backsheet 20 covers the absorbent structure 14 and preferably extends beyond the absorbent structure 14 toward the longitudinal edges 42 and end edges 44 of the diaper 10 and may be joined with the topsheet 18. The backsheet 20 prevents the bodily exudates absorbed by the absorbent structure 14 and contained within the diaper 10 from soiling other external articles that may contact the wearer, such as bed sheets and undergarments. In preferred embodiments, the backsheet 20 is substantially impervious to bodily exudates and comprises a laminate of a nonwoven and a thin plastic film such as a thermoplastic film. The backsheet 20 may comprise breathable materials that permit vapor to escape from the diaper 10 while still preventing bodily exudates from passing through the backsheet 20. It may be semi-rigid, non-elastic and can be made fully or partially elasticized and include backing. The backsheet 20 may be assembled in a variety of well-known configurations and are well known in the art.

The diaper 10 comprises a topsheet 18 that is preferably soft, compliant, exhibits good strikethroughs and has a reduced tendency to rewet from the liquid absorbent material. The topsheet 18 is placed in close proximity to the skin of the wearer when the diaper 10 is worn. In this way, such topsheet 18 permits bodily exudates to rapidly penetrate it so as to flow toward the absorbent structure 14 more quickly, but preferably not allowing such bodily exudates to flow back through the topsheet 18. The topsheet 18 may be constructed from any one of a wide range of liquid and vapor permeable, preferably hydrophilic, materials. The upper and lower surface of the topsheet 18 may be treated differently and may for instance include a surfactant on the upper surface so as to facilitate liquid transfer there through, especially at a central zone or area of the topsheet 18 located over the absorbent structure 14, and for instance include a hydrophobic agent on the lower surface to minimize the liquid contained within the absorbent core from contact wetting the topsheet 18 thereby reducing rewet values. The topsheet 18 may also be coated with a substance having rash preventing or rash reducing properties (e.g. aloe vera). The topsheet 18 covers substantially the entire wearer facing area of the diaper 10, including substantially all of the front waist region 30, back waist region 32, and crotch region 34. Further, the side panels 22 and/or waist feature layers of the inner region may be formed from the same single topsheet material and, thus, may be referred to as being unitary with the topsheet 18 in forming longitudinal and lateral extensions of the top sheet 18 material. Alternatively, the topsheet 18 may be formed from multiple different materials which vary across the width of the topsheet 18. Such a multiple piece design allows for creation of preferred properties and different zones of the topsheet 18. The topsheet 18 may be semi-rigid, non-elastic and can be made fully or partially elasticized. The topsheet 18 may be assembled in a variety of well-known configurations and are well known in the art.

The absorbent structure 14 in FIG. 1 generally is disposed between the topsheet 18 and the backsheet 20. The absorbent structure 14 may comprise any absorbent material that is generally compressible, conformable, non-irritating to the wearer's skin, and capable of absorbing and retaining bodily exudates. The absorbent structure 14 may comprise a wide variety of liquid absorbent materials commonly used in absorbent articles. The absorbent structure 14 according to various embodiments of the invention may be configured to extend substantially the full length and/or width of the diaper 10. However, alternatively the absorbent structure 14 according to the invention is not coextensive with the entire diaper 10 and is limited to certain regions of the diaper 10 such as for instance the crotch region 34. In various embodiments, the absorbent structure 14 extends to the edges of the diaper 10 and the absorbent material is concentrated in the crotch region 34 or another target zone of the diaper 10. In still another embodiment, the particles can be a combination of absorbent material, preferably comprising absorbent polymer material, and skin care particles such as ion exchange resins, deodorant, anti-microbial agents, binder particles, or other beneficial particles. The absorbent structure 14 is displayed as having a substantially rectangular configuration, however, the absorbent structure can also comprise other shapes known in the art such as, elliptical shaped, dogbane shaped, T-shaped or I-shaped configurations.

The diaper 10 may also utilize a pair of containment walls or cuffs 24. Each cuff 24 is a longitudinally extending wall structure preferably positioned on each side of the absorbent structure 14 and spaced laterally from the longitudinal axis 36. The longitudinal ends of the cuffs 24 may be attached or joined, for example, to the topsheet 18 in the front and rear waist regions 30 and 32. Preferably, the ends of the cuffs 24 are tacked down inwardly and attached, for example, by adhesive or sonic bonding to the lower structure. Such a construction effectively biases the cuffs 24 inwardly and is generally considered to cause the cuffs 24 to exhibit improved leakage prevention properties. Preferably, the cuffs 24 are equipped with elastic members 28, which extend along a placed within the cuffs 24, preferably at the top of the cuff 24 while in a stretched condition and then glued or sonic bonded to the cuff 24 at least at their ends. When released or otherwise allowed relaxing, the elastic members 28 retract inwardly. When the diaper 10 is worn, the elastic members 28 function to contract the cuffs 24 about the buttocks and the thighs of the wearer in a manner, which forms a seals between the diaper 10, the buttocks and the thighs. The cuffs 24 may be assembled in a variety of well-known configurations and are well known in the art.

The diaper 10 may also employ additional layers including an acquisition layer and/or dispersion layer situated between the topsheet and the absorbent core and/or coverstock layers. This serves to slow down the flow so that the liquid has adequate time to be absorbed by the absorbent core.

In order to keep the diaper 10 in place about the wearer, preferably at least a portion of the back waist region 32 is attached by fastening or securing members 46 to at least a portion of the front waist region 30, preferably to form leg openings and an absorbent article waist. Fastening or securing members 46 carry the tensile load around the absorbent article waist and compliment the elastic members 28 by providing a quasi-seal between the wearer, the elastic waist feature 26 and cuffs 24, so that bodily exudates are contained within the diaper 10 which are then absorbed. In other words, so that it does not leak through gaps between the wearer and the edge of the diaper 10. The fastening or securing members 46 may for instance be adhesive, mechanical fasteners, hook and loop features, conceivable strings anti/or combinations thereof, i.e., anything that will secure one end of the diaper 10 to the longitudinally opposite end of the diaper 10. The fastening or securing members 46 may also be co-adhesive such that they adhere to each other but not other materials. The fastening or securing members 46 and any component thereof may include any material suitable for such a use, including but not limited to plastics, films, foams, non-woven webs, woven webs, paper, laminates, fiber reinforced plastics and the like, or combinations thereof. It may be preferable that the materials making up the fastening or securing members 46 are flexible, extensible and/or elastic, allowing them to better conform to the shape and movements of the body and thus, reduces the likelihood that the fastening system will irritate or injure the wearer's skin. Preferably, the diaper 10 is affixed to the wearer by tape fasteners which are permanently affixed to the backsheet 20. Tape fasteners are contacted with the transversely opposite side panel or ears 22 attached or joined and extending from the backsheet 20, where they remain affixed due to the binding compound applied to the fasteners. Alternatively, the absorbent article may be pants and the like. In this configuration, the absorbent article may or may not have tape fasteners. Specific disposability tapes may however also be provided on such absorbent articles. All fastening and securing elements 46 may be assembled in a variety of well-known configurations and are well known in the art.

The waist regions 30 and 32 each comprise a central region and a pair of side panels or ears 22 which typically comprise the outer lateral portions of the waist regions. These side panels 22 may be unitary with the chassis 12 and/or backsheet 20 or may be attached or joined thereto by any means know in the art. In a preferred embodiment of the present invention, the side panels 22 positioned in the back waist region 32 are flexible, extensible and/or elastic in at least the lateral direction (i.e., elasticized side panels), in another embodiment the side panels 22 are non-elastic, semi-rigid, rigid and/or stiff. These varieties of side panels 22 are well known in the art.

Furthermore waistbands 26 employing elastic members can be positioned along the transverse portion of the diaper 10 so that when worn, the waistbands 26 are positioned along the waist of the wearer. Generally, the waistband 26 preferably creates a seal against the waist so that bodily exudates do not leak from the regions between the elastic waistband 26 and the waist of the wearer. Although the bodily exudates are primarily absorbed by the absorbent materials within the diaper 10, the seal is important considering the assault of liquid by the wearer may overwhelm the absorption rate capacity of the absorbent structure 14. Hence, the waistbands 26 contain the liquid while it is being absorbed, they are well known in the art.

The absorbent article such as a diaper 10 may also include such other features, components and elements as are known in the art including front and rear ear panels, waist cap features, elastics and the like to provide better fit, containment and aesthetic characteristics. These features may be assembled in a variety of well-known configurations and are well known in the art.

EXAMPLES

Figure 2:
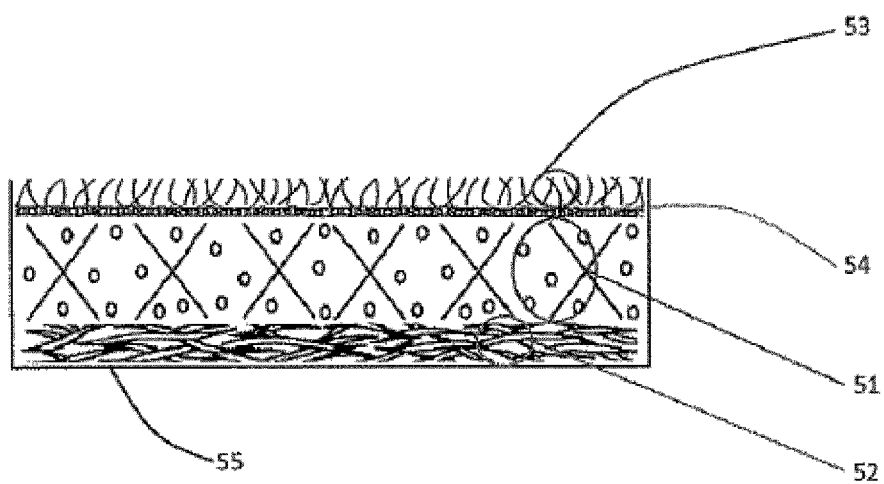
FIG. 2 provides a cross-sectional schematic illustration of an absorbent structure according to a preferred embodiment of the current invention.

An exemplary embodiment of the absorbent structure is illustrated in FIG. 2. From top to bottom, the structure comprises an acquisition layer (53), a dispersion layer (54), an absorbent core (51) with fibers and absorbent polymer materials, a release structure (52) and a wicking and edge barrier (55). The acquisition layer (53) and the dispersion layer (54) may be unitary or non-unitary with the absorbent core. Also the release structure (52) can be unitary or non-unitary with the absorbent core (51). Moreover, the release structure (52) may be unitary or non-unitary with the wicking and edge barrier (55).

Examples of such preferred and suitable release structures are for instance a super absorbent airlaid of 30-120 gsm, preferably 90-115 gsm, most preferably 95-110 gsm, a viscose of 40-125 gsm, preferably 95-120 gsm, most preferably 100-110 and/or 45/55 Viscose/PET layer of 50-135 gsm, preferably 105-130 gsm, most preferably 115-125 gsm.

An airlaid material of 60-120 gsm would preferably have an average thickness measured according to the WSP 120.6.R4.12 of 1.00-3.00 mm, more preferably 1.25-2.75 mm, even more preferably in between 1.50-2.50 and most preferably around 1.5 to 2 mm. Their dry tensile strength in machine direction according to cN/5 cm would be at least around 30-100, more preferably at least around 62.5-100 and most preferably at least around 75 (WSP 110.4.R4.12). In cross-direction it would preferably be at least around 30-110, more preferably at least around 50-100 and most preferably at least around 60, as measured according to (WSP 110.4.R4.12). Their absorbent capacity would preferably at least 5-10 g/g, preferably at least 15 g/g, more preferably at least 20 g/g, even more preferably at least 25 g/g and most preferably more than 30 g/g or more than 35 g/g. In a preferred airlaid material of 120 gsm their absorbent capacity would preferably at least 500 g/m$^2$, more preferably at least 750 g/m$^2$, even more preferably at least 1000 g/m$^2$, even more preferably 1500 g/m$^2$ and most preferably at least 2000 g/m$^2$ or 3000 g/m$^2$. The absorbent capacity can for instance be measured by WSP 010.1.R3.12.

An 100% viscose material containing 0% polyester of 105-130 gsm would preferably have an average thickness measured according to the WSP 120.6.R4(12) of 0.75-2.50 mm, more preferably 1-2.25 mm, even more preferably in between 1.25-2.00 and most preferably around 1.5 to 1.75 mm. Their dry tensile strength in machine direction would preferably be at least 65, more preferably at least around 75 and most preferably above 85 (WSP 110.4.R4.12). In cross-direction it would preferably be at least around 10-125, more preferably at least around 15-75 and most preferably at least around around 25, as measured according to (WSP 110.4.R4.12). Their absorbent capacity would preferably at least 7.5 g/g, preferably at least 9 g/g, more preferably at least 10 g/g, even more preferably at least 12.5 g/g and most preferably more than 15 g/g or more than 20 g/g. In a preferred viscose material of 125 gsm their absorbent capacity would preferably be at least 250 g/m$^2$, more preferably at least 500 g/m$^2$, even more preferably at least 750 g/m$^2$, even more preferably 1000 g/m$^2$ and most preferably at least 1500 g/m$^2$ or 2500 g/m$^2$. The absorbent capacity can for instance be measured by WSP 010.1.R3.12.

An viscose/PET material containing 45% viscose and 55% PET of 70-125 gsm would preferably have an average thickness measured according to the WSP 120.6.R4(12) of 0.50-2.50 mm, more preferably 0.75-2.25 mm, even more preferably in between 0.75-2.00 and most preferably around 1 to 2 mm. Their dry tensile strength in machine direction according to cN/5 cm would be at least around cN/5 cm would be at least around 40, more preferably at least around 60 and most preferably above 75 (WSP 110.4.R4.12). In cross-direction it would preferably be at least around 10-100, more preferably at least around 15-75 and most preferably at least around 20 as measured according to WSP 110.4.R4.12. Their absorbent capacity would preferably at least 5 g/g, preferably at least 7 g/g, more preferably at least 10 g/g, even more preferably at least 12.5 g/g and most preferably more than 15 g/g or more than 20 g/g. In a preferred material of 125 gsm their absorbent capacity would preferably at least 150 g/m$^2$, more preferably at least 300 g/m$^2$, even more preferably at least 600 g/m$^2$, even more preferably 900 g/m$^2$ and most preferably at least 1250 g/m$^2$ or 2000 g/m$^2$. The absorbent capacity can for instance be measured by WSP 010.1.R3.12.

According to an embodiment, the release structure comprises a nonwoven with a weight of at least 10 gsm, preferably at least 20 gsm, more preferably at least 35 gsm, and most preferably at least 50 gsm. A preferred exemplary release structure comprises a spunlace nonwoven and has a weight of 55 gsm, having an absorption capacity of at least 250 g/m$^2$.

According to an embodiment the release structure exhibits high instantaneous water holding capacity (IWHC). IWHC of a release structure or any other component of an absorbent article can be divided in a static IWHC and a dynamic IWHC. Within the meaning of this application a release structure or any other component of the absorbent article is said to have a high IWHC when at least one of the static IWHC and the dynamic IWHC of said release structure or other component is above a corresponding predefined static IWHC threshold and/or predefined dynamic IWHC threshold, respectively. IWHC can be measured according to the following two IWHC test procedures, which will be described below, in view of the test setup as schematically illustrated in FIG. 36.

Static IWHC Test

This test measures the amount of test liquid which runs down a test sample when a specified mass of test liquid is poured on the test sample which is positioned on an inclined plane. This test is a variation of the nonwoven standard procedure for measuring run-off (NWSP 080.9.R0 (15)) and is designed to measure and compare the static IWHC of different test samples.

Figure 36:
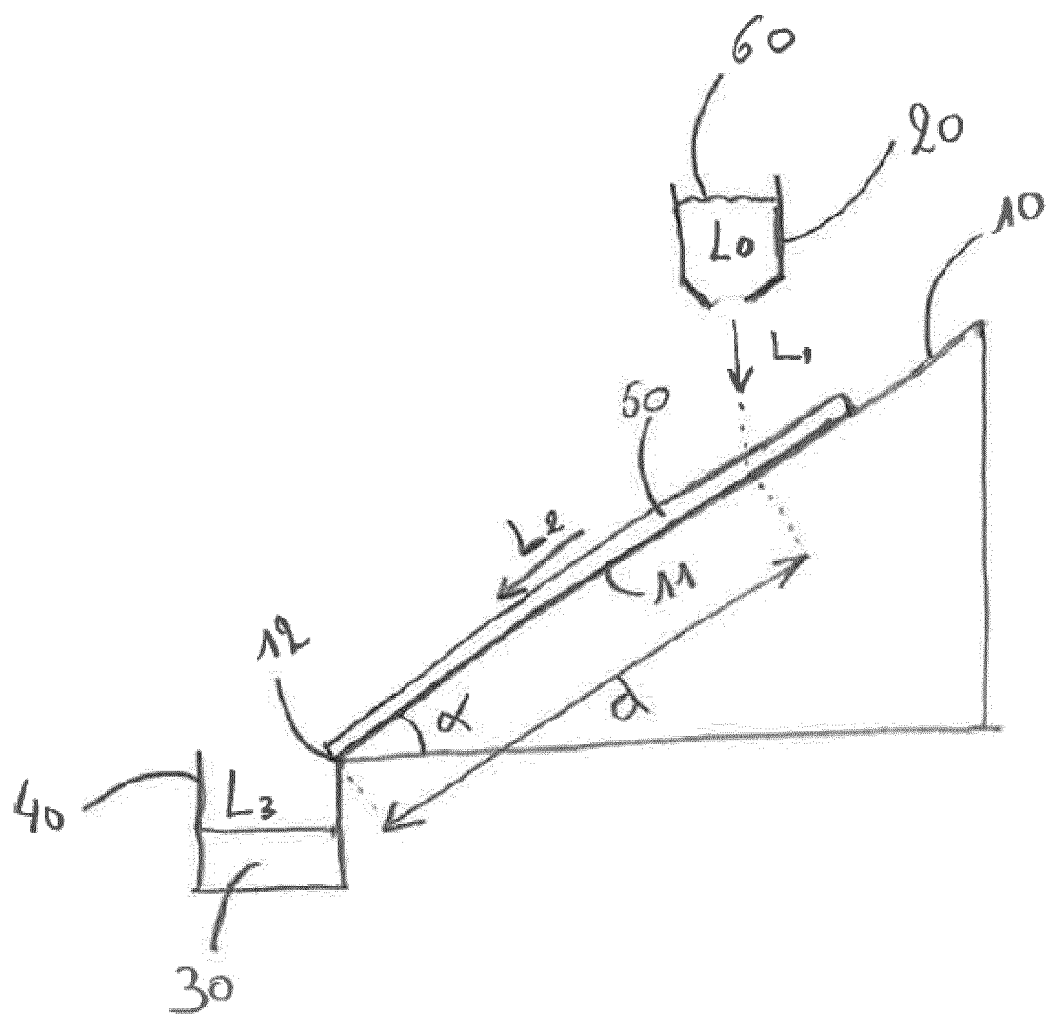
FIG. 36 illustrates schematically a IWHC test setup.

The static IWHC test setup is illustrated in FIG. 36 and comprises:
- a run-off table 10 comprising a run-off surface 11 which is inclined according to a slope angle α and is configured for positioning thereon a test sample 50 with predefined dimensions;
- a dosing device 20 which is capable of delivering 30±0.5 g of test liquid 60 to the test sample 50 in a continuous stream at a rate of 2±0.2 ml/s;
- a recipient 40 for receiving test liquid 60 which leaks from the test sample 50; and
- weighing means 30 which are capable of determining a mass of 30±0.01 g, for determining an amount of test liquid 60 that has leaked into the recipient 40.

The run-off table 10 may be made of acrylic glass or a similar material and preferably has a slope angle α which can be varied.

The dosing device 20 may for example be a known dosing device such as defined by Hy-Tec labs, Haan, Germany which is capable to deliver the test liquid 60 in a continuous stream via the bottom opening thereof at a rate of 2 ml/s. Alternatively other dosing devices may be used which e.g. comprise a funnel or a syringe with a motorized syringe drive. Preferably, the dosing device 20 is provided with a hydraulic, pump or other pressurized system which is attached to the dosing device, in a manner such that no leaks occur between the dosing device 20 and said hydraulic, pump or other pressurized system.

The recipient 40 may be any kind of container which is designed to receive and hold the test liquid which leaks from the test sample 50. To achieve the below test results a simple tray was used, however, other recipients 40 may be used e.g. a standard receiver pad as used in NWSP 080.9.R0 (15).

The weighing means 30 may be an analytical balance which is capable of determining a mass of 30±0.01 g, for determining an amount of test liquid 60 that has leaked into the recipient 40.

As test liquid 60, simulated urine was used, which consists of a 9 g/l solution of sodium chloride in distilled water. Preferably the test liquid 60 has a surface tension of 70±2 mN/m. Test liquid is at room temperature of 25±1° C.

The test sample 50 has predefined dimensions. To achieve the below test results, the test samples have been prepared to have a length of 360 mm and a width of 100 mm. The test sample is then positioned and fixed on the run-off surface 11 of the run-off table 10 such that an edge of the test sample coincides with the bottom edge 12 of the run-off table 10. The entire surface of the test sample is supported by the run-off surface 11 of the run-off table. The dosing device 20 is positioned above the test sample 50 which is located on the run-off surface 11 such that delivered test liquid 60 from the dosing device 20 to the test sample 50 has to travel 300 mm along the length of the test sample 50 in the direction of the bottom edge 12 of the run-off table 10 before leaking into the recipient 40. The dosing device 20 is positioned above the test sample 50 such that the test liquid travels a distance of 45±3 mm, along arrow L1, before reaching the test sample 50.

For keeping time during the test procedure a timer is used which is capable of measuring a time of 180 s with an accuracy of 0.1 s.

The static IWHC test procedure is carried out using the above described setup and by:
- setting the slope angle α to 30±1°;
- using a standard quantity of 30 ml of test liquid 60;
- starting delivery of test liquid to the test sample with a rate of 2 ml/s and start timer;
- measuring leakage mass (in g), which is the mass of test liquid 60 which has dripped out of the test sample 50 and into the recipient 40;
- recording the leakage mass at predefined time intervals, e.g. intervals of 10 s between 0 s and 180 s;
- calculating a mean leakage mass (Ls) using the formula:

$$Ls = (0.6 \times \text{leakage mass at 30 s}) + (0.3 \times \text{leakage mass at 60 s}) + (0.1 \times \text{leakage mass at 120 s});$$

- calculating static IWHC (IWHCs) using the formula: IWHCs=30−Ls; and
- calculating IWHCs percentage (IWHCs %) using the formula: IWHCs/30.

During the above described test procedure test liquid 60 is delivered, from its starting position L0 in the dosing device 20, to the test sample 50. As soon as the first amount of test liquid 60 reaches the test sample 50, the timer is started. Delivery of the first amount of test liquid 60 to the test sample 50 may be detected in various ways, e.g. by visual inspection, by means of a pressure sensor, by means of an electronical sensor, etc. Test liquid 60 is delivered to the test sample as indicated by arrow L1 in FIG. 36. The test liquid 60 is then transported through the test sample in the direction of arrow L2, being subjected to gravity. When the test liquid 60 reaches the edge of the test sample 50 which coincides with the bottom edge 12 of the run-off table 10, the test liquid will leak into the recipient 40 to reach its end position L3.

According to an embodiment, the release structure exhibits a static IWHC percentage (IWHC %) of at least 30%, preferably at least 40%, more preferably at least 50%, and most preferably at least 60%.

Dynamic IWHC Test

This test measures the amount of test liquid which runs down a test sample when a substantially continuous supply of test liquid is poured on the test sample at a predefined rate. This test is a variation of the nonwoven standard procedure for measuring run-off (NWSP 080.9.R0 (15)) and is designed to measure and compare the dynamic IWHC of different test samples.

The dynamic IWHC test setup is essentially the same as the static IWHC test setup as illustrated in FIG. 36 and described above. The main difference in setup is that the dosing device 20 is configured to provide a substantially continuous supply of test liquid in stead of delivering the predefined supply of 30 ml of test liquid. To this end the dosing device 20 may be provided with a dosing pump.

The dynamic IWHC test procedure is carried out using the dynamic IWHC test setup and by:
- setting the slope angle α to 30±1°;
- setting the dosing device to deliver test liquid at a rate of 3±0.3 ml/s;

starting dosing pump, and subsequently start timer as soon as the first amount of test liquid 60 reaches the test sample 50;

measuring leakage mass (in g), which is the mass of test liquid 60 which has dripped out of the test sample 50 and into the recipient 40;

stopping the dosing pump when a first amount of test liquid 60 leaks out of the test sample 50 and into the recipient 40, and record the time TL (s) as Time until Leakage;

measuring leakage mass (in g), which is the mass of test liquid 60 which has dripped out of the test sample 50 and into the recipient 40;

recording the leakage mass at predefined time intervals, e.g. intervals of 1 s between 0 s and 30 s, and intervals of 10 s between 30 s and 180 s;

calculating a mean leakage mass (Ls) using the formula:

$Ls=(0.4\times\text{leakage mass at } 30 \text{ s})+(0.3\times\text{leakage mass at } 60 \text{ s})+(0.2\times\text{leakage mass at } 120 \text{ s})+(0.1\times\text{leakage mass at } 180 \text{ s})$; and calculating dynamic IWHC (IWHCd) using the formula:

$IWHCd=\text{weight of wet test sample } Ww \text{ (g)}-\text{weight of dry test sample } Wd \text{ (g)}$ The weight of the dry test sample is measured before starting the delivery of test liquid to the test sample, whereas the weight of the wet test sample is measured 180 s after first leakage has occurred on the test sample.

During the above described test procedure test liquid 60 is delivered, from its starting position L0 in the dosing device 20, to the test sample 50. As soon as the first amount of test liquid 60 reaches the test sample 50, the timer is started. Delivery of the first amount of test liquid 60 to the test sample 50 may be detected in various ways, e.g. by visual inspection, by means of a pressure sensor, by means of an electronical sensor, etc. Test liquid 60 is delivered to the test sample as indicated by arrow L1 in FIG. 36. The test liquid 60 is then transported through the test sample in the direction of arrow L2, being subjected to gravity. When the test liquid 60 reaches the edge of the test sample 50 which coincides with the bottom edge 12 of the run-off table 10, the test liquid will leak into the recipient 40 to reach its end position L3.

According to an embodiment, the release structure exhibits a dynamic IWHC, IWHCd, of at least 4 g, preferably at least 10 g, more preferably at least 20 g, and most preferably at least 30 g.

Whereas the static IWHC test has been carried out for test samples consisting of raw materials, i.e. types of nonwovens which are candidate materials for being incorporated into a release structure according to the present invention, the dynamic IWHC test has also been carried out for test samples consisting of entire absorbent articles. Test results for a variety of test samples which have been submitted to the static IWHC test and/or the dynamic IWHC test are illustrated below and in FIGS. 37 to 50.

Test Results

Test results of the above described static IWHC test and dynamic IWHC test have been recorded in the tables below, wherein for a variety of test samples the measured time and the corresponding weight of the test liquid which has leaked into the recipient are listed. Static IWHC tests have been conducted on test samples of material layers as used in an absorbent article, whereas dynamic IWHC test have been conducted on test samples of material layers as used in an absorbent article, and on test samples of actual absorbent articles, thus comprising multiple layers of materials.

Static IWHC Test—Core Wrap 8 gsm

| time [s] | weight [g] |
| --- | --- |
| 10 | 7.6 |
| 20 | 19.6 |
| 30 | 22.1 |
| 40 | 22.6 |
| 50 | 22.8 |
| 60 | 22.9 |
| 70 | 23.1 |
| 80 | 23.1 |
| 90 | 23.2 |
| 100 | 23.3 |
| 110 | 23.3 |
| 120 | 23.4 |
| 130 | 23.4 |
| 140 | 23.4 |
| 150 | 23.5 |
| 160 | 23.5 |
| 170 | 23.5 |
| 180 | 23.5 |
| 190 | 23.6 |
| 200 | 23.6 |
| 210 | 23.7 |
| 220 | 23.7 |
| 230 | 23.7 |
| 240 | 23.7 |
| 250 | 23.7 |
| 260 | 23.7 |
| 270 | 23.8 |
| 280 | 23.8 |
| 290 | 23.8 |
| 300 | 23.8 |
| 310 | 23.8 |
| 320 | 23.8 |
| 330 | 23.8 |
| 340 | 23.8 |
| 350 | 23.9 |
| 360 | 23.9 |
| 370 | 23.9 |
| 380 | 23.9 |
| 390 | 23.9 |
| 400 | 23.9 |
| 410 | 23.9 |
| 420 | 23.9 |

Figure 37:
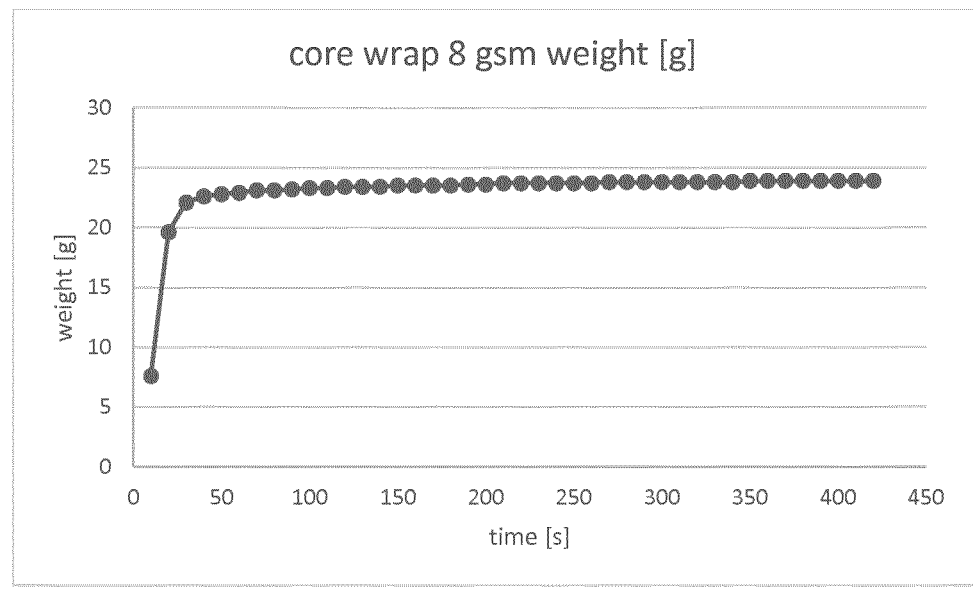

These measurements are further illustrated in the graph of FIG. 37 and lead to a IWHCs of 7, 53 and a corresponding IWHCs % of 25% for the core wrap 8 gsm test sample.

Static IWHC Test—Spunlace 125 gsm

| time [s] | weight [g] |
| --- | --- |
| 10 | 0.0 |
| 20 | 0.0 |
| 30 | 0.0 |
| 40 | 0.0 |
| 50 | 0.0 |
| 60 | 0.0 |
| 70 | 0.0 |
| 80 | 0.0 |
| 90 | 0.0 |
| 100 | 0.0 |
| 110 | 0.0 |
| 120 | 0.0 |
| 130 | 0.0 |
| 140 | 0.0 |
| 150 | 0.0 |
| 160 | 0.0 |
| 170 | 0.0 |
| 180 | 0.0 |
| 190 | 0.0 |
| 200 | 0.0 |
| 210 | 0.0 |
| 220 | 0.0 |
| 230 | 0.0 |

| time [s] | weight [g] |
| --- | --- |
| 240 | 0.0 |
| 250 | 0.0 |
| 260 | 0.0 |
| 270 | 0.0 |
| 280 | 0.0 |
| 290 | 0.0 |
| 300 | 0.0 |
| 310 | 0.0 |
| 320 | 0.0 |
| 330 | 0.0 |
| 340 | 0.0 |
| 350 | 0.0 |
| 360 | 0.0 |
| 370 | 0.0 |
| 380 | 0.0 |
| 390 | 0.0 |
| 400 | 0.0 |
| 410 | 0.0 |
| 420 | 0.0 |

Figure 38:
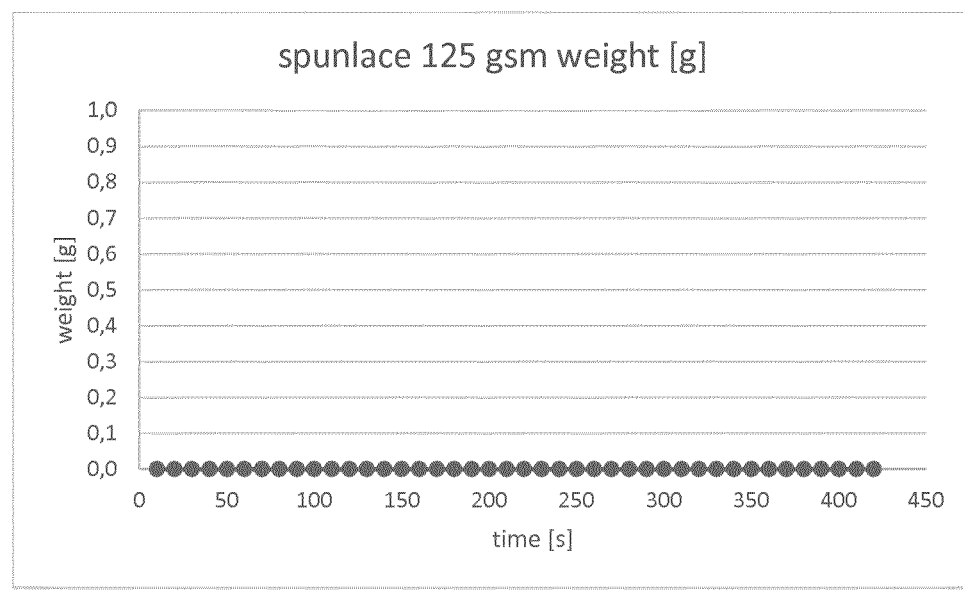

These measurements are further illustrated in the graph of FIG. 38 and lead to a IWHCs of 30 and a corresponding IWHCs % of 100% for the spunlace 125 gsm test sample. In other words, no test liquid has leaked from the test sample.

Static IWHC Test—Highloft 60 gsm

| time [s] | weight [g] |
| --- | --- |
| 10 | 0.0 |
| 20 | 0.0 |
| 30 | 5.2 |
| 40 | 8.0 |
| 50 | 9.4 |
| 60 | 10.3 |
| 70 | 10.8 |
| 80 | 11.2 |
| 90 | 11.5 |
| 100 | 11.7 |
| 110 | 11.9 |
| 120 | 12.1 |
| 130 | 12.2 |
| 140 | 12.3 |
| 150 | 12.3 |
| 160 | 12.4 |
| 170 | 12.5 |
| 180 | 12.5 |
| 190 | 12.6 |
| 200 | 12.6 |
| 210 | 12.7 |
| 220 | 12.7 |
| 230 | 12.7 |
| 240 | 12.7 |
| 250 | 12.8 |
| 260 | 12.8 |
| 270 | 12.8 |
| 280 | 12.8 |
| 290 | 12.9 |
| 300 | 12.9 |
| 310 | 12.9 |
| 320 | 12.9 |
| 330 | 12.9 |
| 340 | 12.9 |
| 350 | 12.9 |
| 360 | 13.0 |
| 370 | 13.0 |
| 380 | 13.0 |
| 390 | 13.0 |
| 400 | 13.0 |
| 410 | 13.0 |
| 420 | 13.0 |

Figure 39:
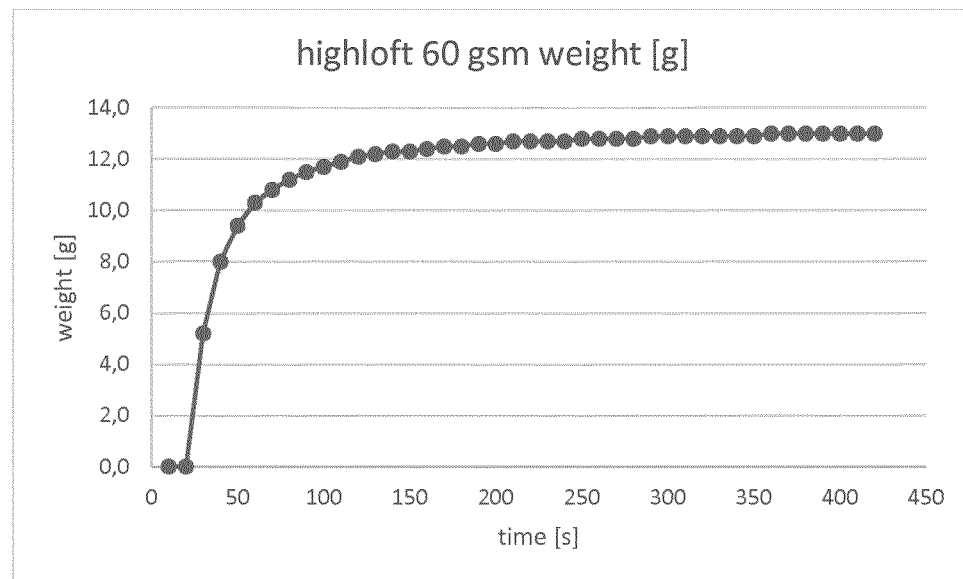

These measurements are further illustrated in the graph of FIG. 39 and lead to a IWHCs of 22,58 and a corresponding IWHCs % of 75% for the highloft 60 gsm test sample.

Static IWHC Test—Airlaid 55 gsm

| time [s] | weight [g] |
| --- | --- |
| 10 | 0.0 |
| 20 | 0.4 |
| 30 | 6.0 |
| 40 | 6.8 |
| 50 | 7.5 |
| 60 | 7.9 |
| 70 | 8.3 |
| 80 | 8.5 |
| 90 | 8.8 |
| 100 | 8.9 |
| 110 | 9.1 |
| 120 | 9.2 |
| 130 | 9.3 |
| 140 | 9.4 |
| 150 | 9.4 |
| 160 | 9.5 |
| 170 | 9.5 |
| 180 | 9.6 |
| 190 | 9.6 |
| 200 | 9.6 |
| 210 | 9.7 |
| 220 | 9.7 |
| 230 | 9.7 |
| 240 | 9.7 |
| 250 | 9.8 |
| 260 | 9.8 |
| 270 | 9.8 |
| 280 | 9.8 |
| 290 | 9.8 |
| 300 | 9.8 |
| 310 | 9.8 |
| 320 | 9.8 |
| 330 | 9.9 |
| 340 | 9.9 |
| 350 | 9.9 |
| 360 | 9.9 |
| 370 | 9.9 |
| 380 | 9.9 |
| 390 | 9.9 |
| 400 | 9.9 |
| 410 | 9.9 |
| 420 | 9.9 |

Figure 40:
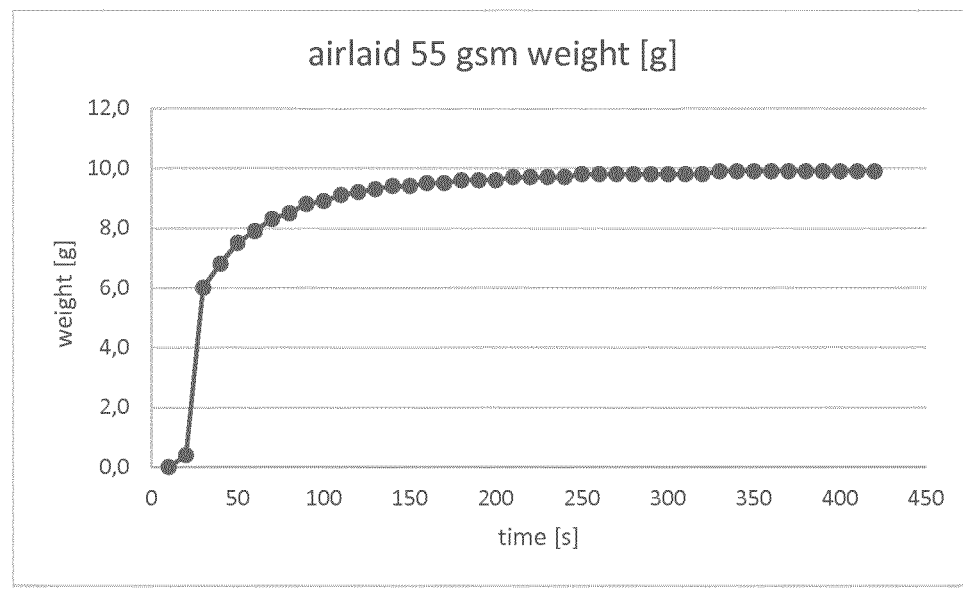

These measurements are further illustrated in the graph of FIG. 40 and lead to a IWHCs of 23,12 and a corresponding IWHCs % of 77% for the airlaid 55 gsm test sample.

Static IWHC Test—Airlaid 60 gsm

| time [s] | weight [g] |
| --- | --- |
| 10 | 0.0 |
| 20 | 0.0 |
| 30 | 0.0 |
| 40 | 0.8 |
| 50 | 1.8 |
| 60 | 2.6 |
| 70 | 3.2 |
| 80 | 3.6 |
| 90 | 3.9 |
| 100 | 4.2 |
| 110 | 4.5 |
| 120 | 4.7 |
| 130 | 4.9 |
| 140 | 5.0 |
| 150 | 5.1 |
| 160 | 5.2 |
| 170 | 5.3 |
| 180 | 5.3 |
| 190 | 5.4 |
| 200 | 5.5 |
| 210 | 5.5 |
| 220 | 5.6 |
| 230 | 5.6 |

| time [s] | weight [g] |
|---|---|
| 240 | 5.7 |
| 250 | 5.7 |
| 260 | 5.8 |
| 270 | 5.8 |
| 280 | 5.8 |
| 290 | 5.8 |
| 300 | 5.8 |
| 310 | 5.9 |
| 320 | 5.9 |
| 330 | 5.9 |
| 340 | 5.9 |
| 350 | 5.9 |
| 360 | 6.0 |
| 370 | 6.0 |
| 380 | 6.0 |
| 390 | 6.0 |
| 400 | 6.0 |
| 410 | 6.0 |
| 420 | 6.0 |

Figure 41:
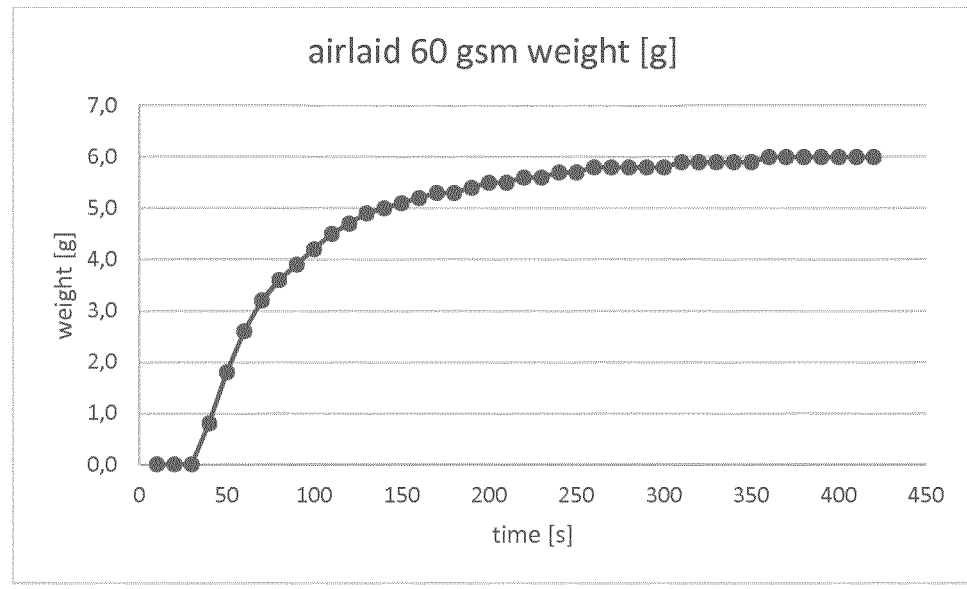

These measurements are further illustrated in the graph of FIG. 41 and lead to a IWHCs of 28,75 and a corresponding IWHCs % of 96% for the airlaid 60 gsm test sample.

Dynamic IWHC Test—Core Wrap 8 gsm

| time [s] | weight [g] |
|---|---|
| 10 | 6.7 |
| 20 | 7.4 |
| 30 | 7.7 |
| 40 | 7.9 |
| 50 | 8.1 |
| 60 | 8.2 |
| 70 | 8.2 |
| 80 | 8.3 |
| 90 | 8.4 |
| 100 | 8.5 |
| 110 | 8.5 |
| 120 | 8.6 |
| 130 | 8.6 |
| 140 | 8.7 |
| 150 | 8.7 |
| 160 | 8.7 |
| 170 | 8.8 |
| 180 | 8.8 |

Weight of Sample

| dry [g] | 0.2 |
|---|---|
| wet [g] | 2.1 |

Figure 42:
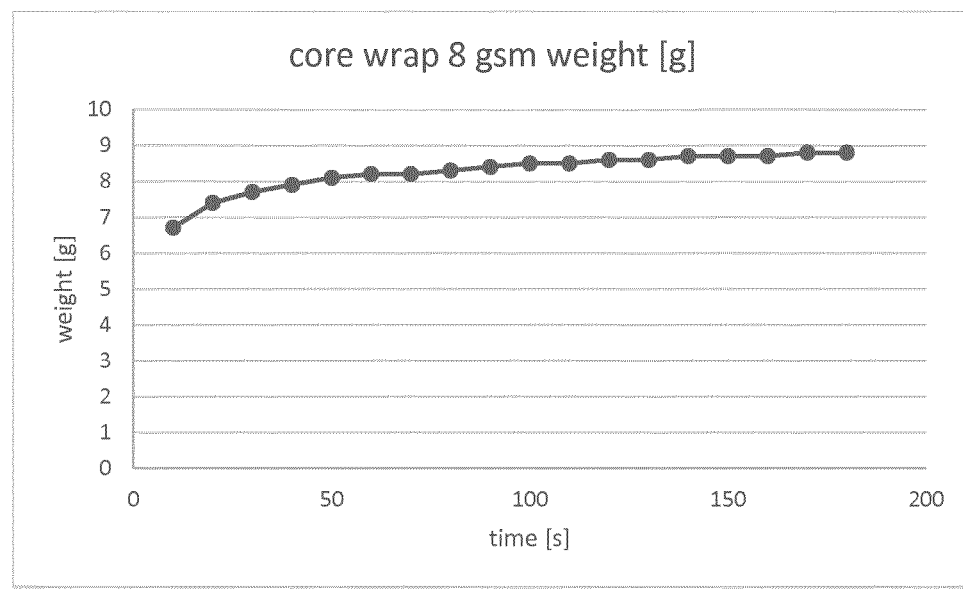

These measurements are further illustrated in the graph of FIG. 42 and lead to a IWHCd of 1,9 for the core wrap 8 gsm test sample.

Dynamite IWHC Test—Spunlace 125 gsm

| time [s] | weight [g] |
|---|---|
| 10 | 7.4 |
| 20 | 8.7 |
| 30 | 9.6 |
| 40 | 10.3 |
| 50 | 10.8 |
| 60 | 11.2 |
| 70 | 11.4 |
| 80 | 11.6 |
| 90 | 11.7 |
| 100 | 11.9 |
| 110 | 12.0 |
| 120 | 12.0 |
| 130 | 12.1 |
| 140 | 12.2 |
| 150 | 12.2 |
| 160 | 12.2 |
| 170 | 12.3 |
| 180 | 12.3 |

Weight of Sample

| dry [g] | 4.1 |
|---|---|
| wet [g] | 35.1 |

Figure 43:
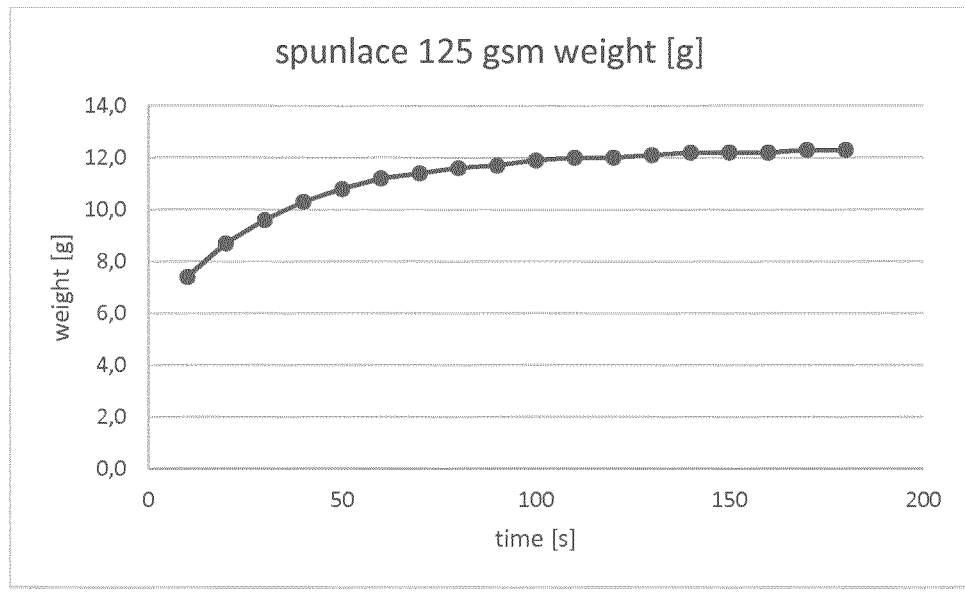

These measurements are further illustrated in the graph of FIG. 43 and lead to a IWHCd of 31,0 for the spunlace 125 gsm test sample.

Dynamic IWHC Test—Highloft 60 gsm

| time [s] | weight [g] |
|---|---|
| 10 | 10.9 |
| 20 | 14.3 |
| 30 | 15.6 |
| 40 | 16.5 |
| 50 | 17.1 |
| 60 | 17.5 |
| 70 | 17.8 |
| 80 | 18.1 |
| 90 | 18.2 |
| 100 | 18.4 |
| 110 | 18.5 |
| 120 | 18.6 |
| 130 | 18.7 |
| 140 | 18.8 |
| 150 | 18.8 |
| 160 | 18.9 |
| 170 | 19.0 |
| 180 | 19.0 |

Weight of Sample

| dry [g] | 2.2 |
|---|---|
| wet [g] | 13.1 |

Figure 44:
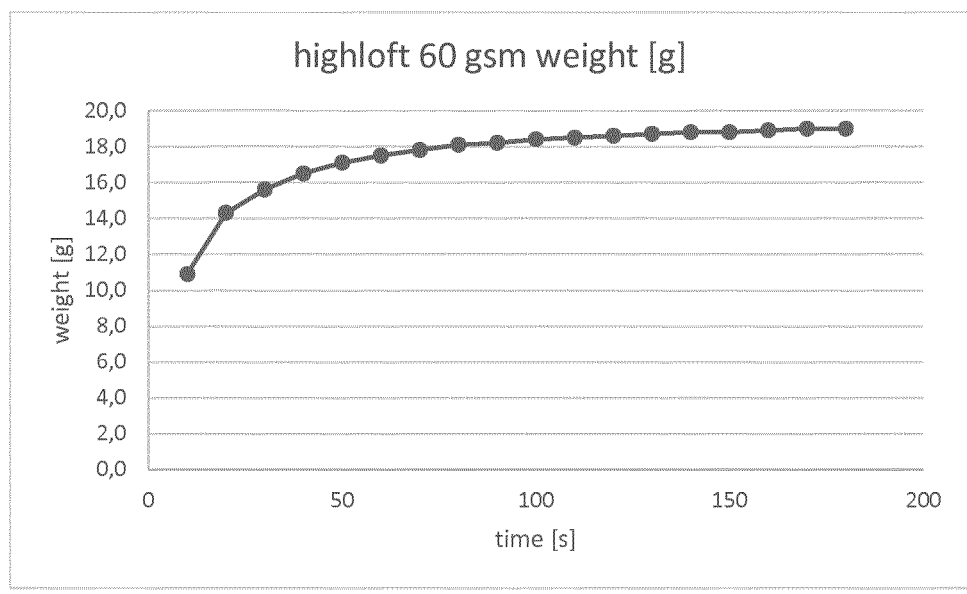

These measurements are further illustrated in the graph of FIG. 44 and lead to a IWHCd of 10,9 for the highloft 60 gsm test sample.

Dynamic IWHC Test—Airlaid 55 gsm

| time [s] | weight [g] |
|---|---|
| 10 | 5.8 |
| 20 | 6.0 |
| 30 | 6.0 |
| 40 | 6.0 |
| 50 | 6.1 |
| 60 | 6.1 |
| 70 | 6.1 |
| 80 | 6.1 |
| 90 | 6.2 |
| 100 | 6.3 |
| 110 | 6.4 |

-continued

| time [s] | weight [g] |
|---|---|
| 120 | 6.4 |
| 130 | 6.4 |
| 140 | 6.4 |
| 150 | 6.5 |
| 160 | 6.5 |
| 170 | 6.5 |
| 180 | 6.5 |

Weight of Sample

| | |
|---|---|
| dry [g] | 2.0 |
| wet [g] | 15.9 |

Figure 45:
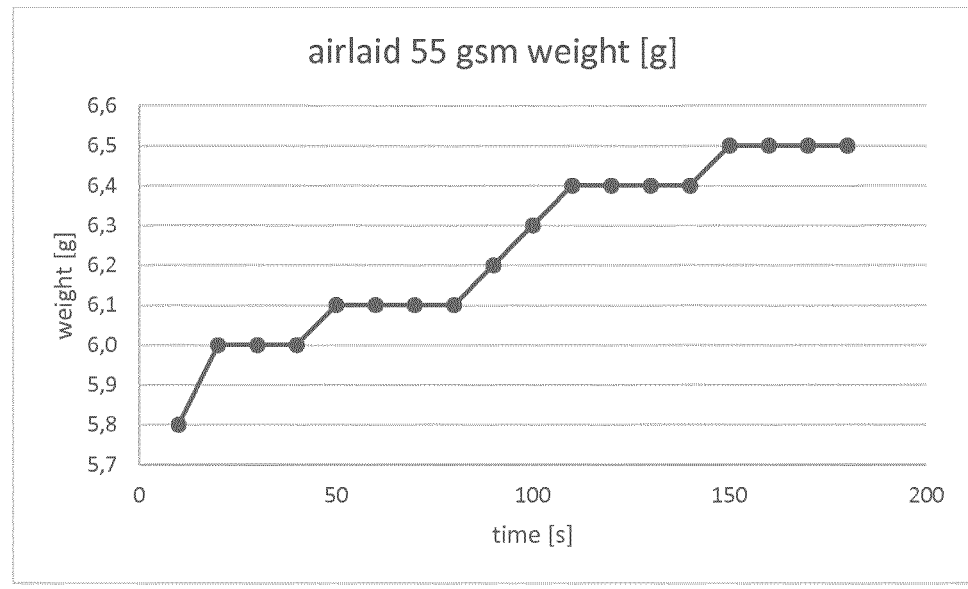

These measurements are further illustrated in the graph of FIG. 45 and lead to a IWHCd of 13,9 for the airlaid 55 gsm test sample.

Dynamic IWHC Test—Airlaid 60 gsm

| time [s] | weight [g] |
|---|---|
| 10 | 5.8 |
| 20 | 6.9 |
| 30 | 7.7 |
| 40 | 8.1 |
| 50 | 8.6 |
| 60 | 8.9 |
| 70 | 9.1 |
| 80 | 9.2 |
| 90 | 9.4 |
| 100 | 9.5 |
| 110 | 9.5 |
| 120 | 9.6 |
| 130 | 9.7 |
| 140 | 9.8 |
| 150 | 9.8 |
| 160 | 9.8 |
| 170 | 9.8 |
| 180 | 9.8 |

Weight of Sample

| | |
|---|---|
| dry [g] | 2.2 |
| wet [g] | 25.6 |

Figure 46:
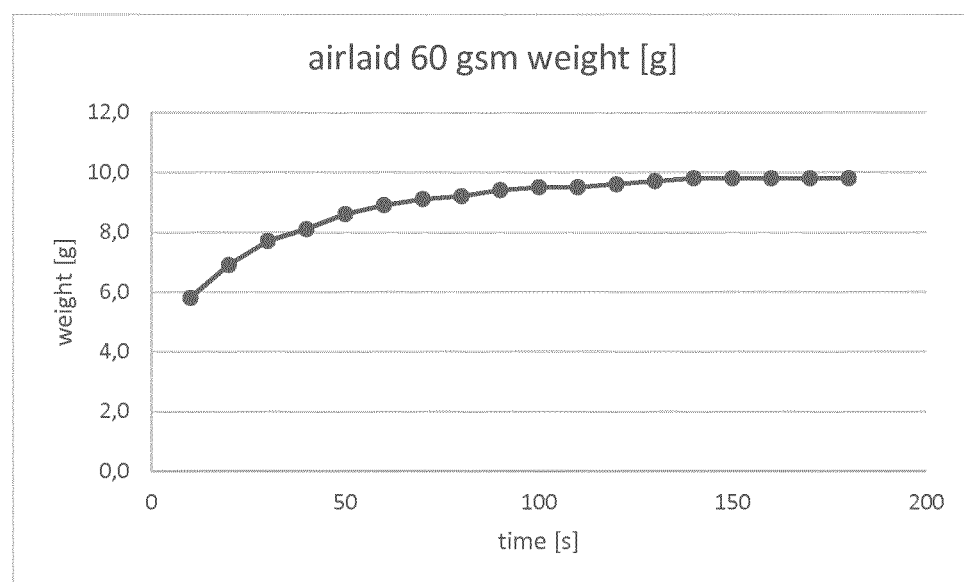

These measurements are further illustrated in the graph of FIG. 46 and lead to a IWHCd of 23,4 for the airlaid 60 gsm test sample.

Dynamic IWHC Test—A-Brand Baby Diaper
First Run

| time [s] | weight [g] |
|---|---|
| 10 | 8.9 |
| 20 | 10.6 |
| 30 | 11.2 |
| 40 | 11.2 |
| 50 | 11.2 |
| 60 | 11.2 |
| 70 | 11.2 |
| 80 | 11.2 |
| 90 | 11.2 |
| 100 | 11.2 |
| 110 | 11.2 |
| 120 | 11.2 |
| 130 | 11.2 |
| 140 | 11.2 |

-continued

| time [s] | weight [g] |
|---|---|
| 150 | 11.2 |
| 160 | 11.2 |
| 170 | 11.2 |
| 180 | 11.2 |

Weight of Sample

| | |
|---|---|
| dry [g] | 16.7 |
| wet [g] | 138.8 |

Figure 47A:
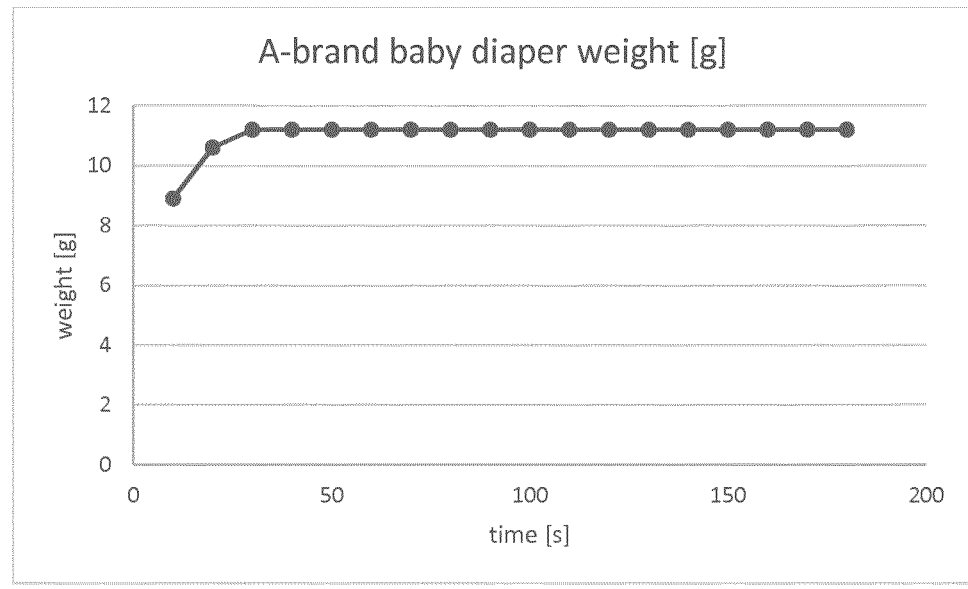
FIG. 47A illustrates dynamic IWHC test results of an "A-brand baby diaper" absorbent article test sample, according to a first test run.

These measurements are further illustrated in the graph of FIG. 47A and lead to a IWHCd of 122,1 for the A-brand baby diaper test sample.

Second Run

| time [s] | weight [g] |
|---|---|
| 10 | 0.0 |
| 20 | 0.0 |
| 30 | 0.0 |
| 40 | 0.0 |
| 50 | 1.2 |
| 60 | 9.1 |
| 70 | 10.4 |
| 80 | 10.6 |
| 90 | 10.6 |
| 100 | 10.6 |
| 110 | 10.6 |
| 120 | 10.6 |
| 130 | 10.6 |
| 140 | 10.6 |
| 150 | 10.6 |
| 160 | 10.6 |
| 170 | 10.6 |
| 180 | 10.6 |
| 190 | 10.6 |
| 200 | 10.6 |
| 210 | 10.6 |
| 220 | 10.6 |
| 230 | 10.6 |
| 240 | 10.6 |
| 250 | 10.6 |
| 260 | 10.6 |
| 270 | 10.6 |
| 280 | 10.6 |
| 290 | 10.6 |
| 300 | 10.6 |

Weight of Sample

| | |
|---|---|
| dry [g] | 16.6 |
| wet [g] | 132.8 |

Figure 47B:
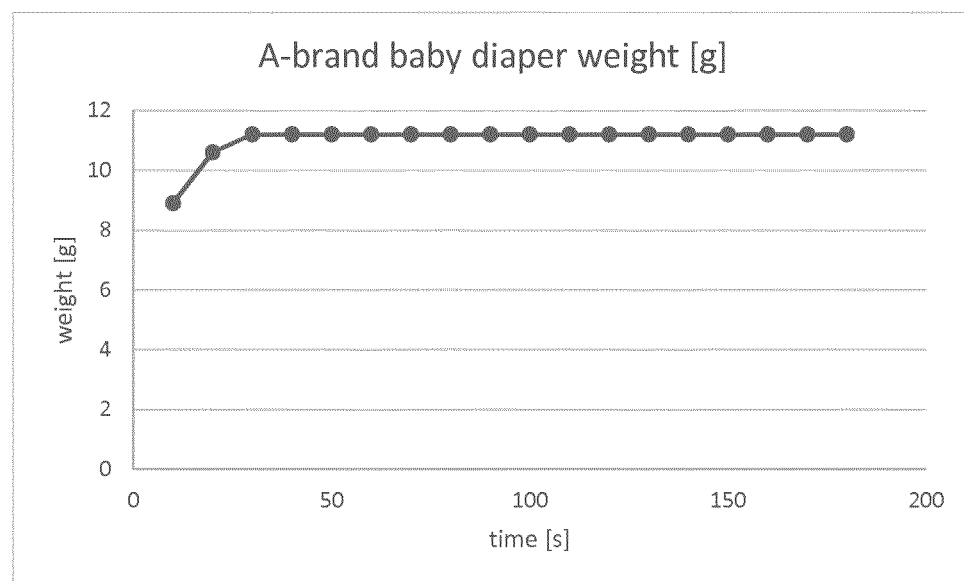
FIG. 47B illustrates dynamic IWHC test results of an "A-brand baby diaper" absorbent article test sample, according to a second test run.

These measurements are further illustrated in the graph of FIG. 47B and lead to a IWHCd of 116,2 for the A-brand baby diaper test sample.

Dynamic IWHC Test—Fluff Pulp Baby Diaper
First Run

| time [s] | weight [g] |
|---|---|
| 10 | 6.8 |
| 20 | 13.9 |
| 30 | 18.6 |
| 40 | 21.3 |
| 50 | 22.7 |

-continued

| time [s] | weight [g] |
|---|---|
| 60 | 23.5 |
| 70 | 23.7 |
| 80 | 23.7 |
| 90 | 23.8 |
| 100 | 23.8 |
| 110 | 23.8 |
| 120 | 23.8 |
| 130 | 23.8 |
| 140 | 23.8 |
| 150 | 23.8 |
| 160 | 23.8 |
| 170 | 23.8 |
| 180 | 23.8 |

Weight of Sample

| dry [g] | 37.9 |
|---|---|
| wet [g] | 429.2 |

Figure 48A:
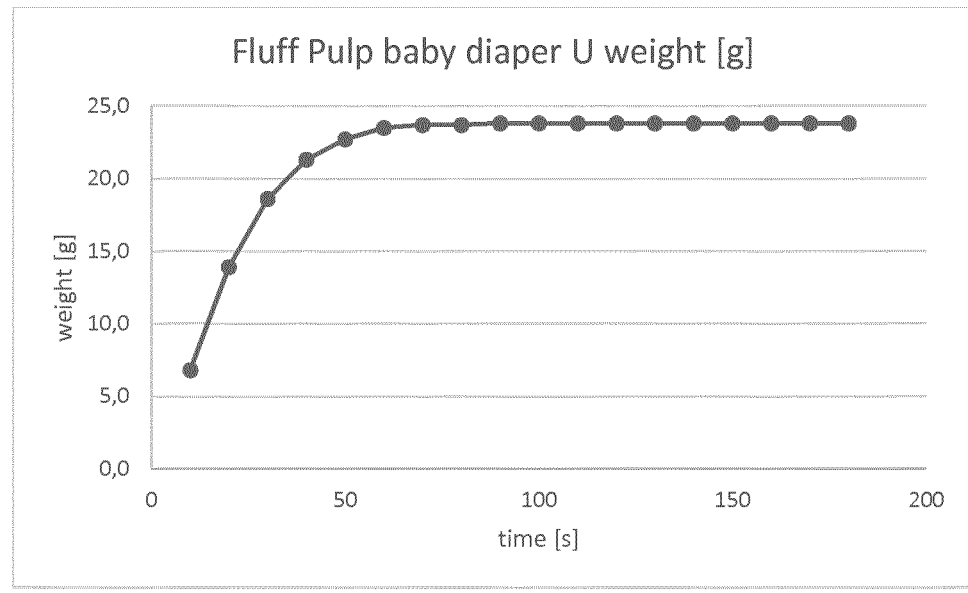
FIG. 48A illustrates dynamic IWHC test results of a "Fluff Pulp" absorbent article test sample, according to a first test run.

These measurements are further illustrated in the graph of FIG. 48A and lead to a IWHCd of 391,3 for the Fluff Pulp baby diaper test sample.

Second Run

| time [s] | weight [g] |
|---|---|
| 10 | 0.0 |
| 20 | 0.0 |
| 30 | 0.0 |
| 40 | 0.0 |
| 50 | 0.0 |
| 60 | 0.0 |
| 70 | 0.0 |
| 80 | 0.0 |
| 90 | 0.0 |
| 100 | 0.0 |
| 110 | 0.0 |
| 120 | 0.0 |
| 130 | 0.0 |
| 140 | 0.0 |
| 150 | 0.0 |
| 160 | 0.0 |
| 170 | 0.0 |
| 180 | 2.1 |
| 190 | 12.7 |
| 200 | 21.4 |
| 210 | 25.1 |
| 220 | 27.1 |
| 230 | 28.6 |
| 240 | 28.7 |
| 250 | 28.9 |
| 260 | 28.9 |
| 270 | 29.0 |
| 280 | 29.0 |
| 290 | 29.0 |
| 300 | 29.0 |
| 310 | 29.0 |
| 320 | 29.0 |
| 330 | 29.0 |
| 340 | 29.0 |
| 350 | 29.0 |
| 360 | 29.0 |
| 370 | 29.0 |
| 380 | 29.0 |
| 390 | 29.0 |
| 400 | 29.0 |

Weight of Sample

| dry [g] | 35.6 |
|---|---|
| wet [g] | 461.9 |

Figure 48B:
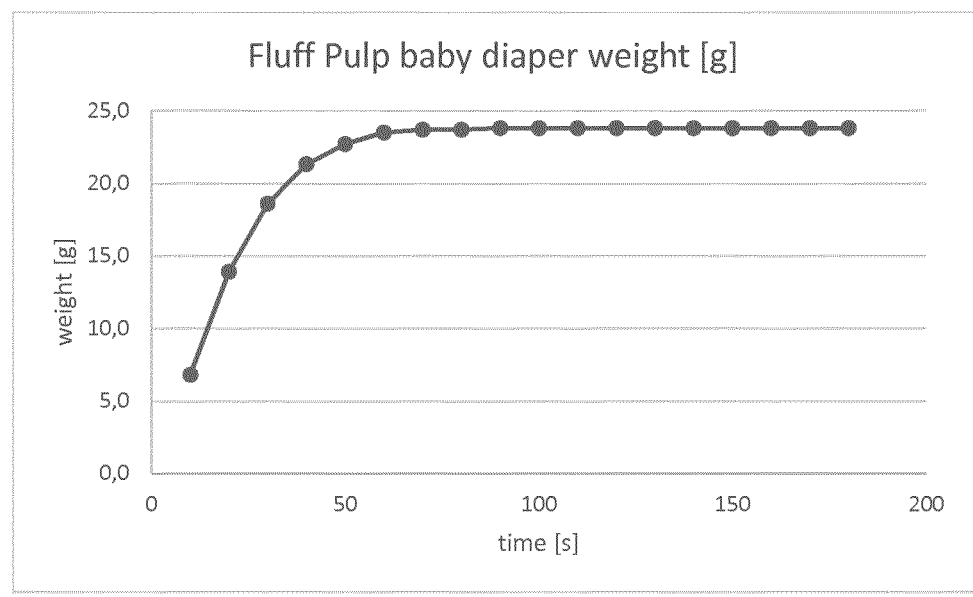
FIG. 48B illustrates dynamic IWHC test results of a "Fluff Pulp" absorbent article test sample, according to a second test run.

These measurements are further illustrated in the graph of FIG. 48B and lead to a IWHCd of 426,3 for the Fluff Pulp baby diaper test sample.

Dynamic IWHC Test—Fluffless Baby Diaper

First Run

| time [s] | weight [g] |
|---|---|
| 10 | 5.8 |
| 20 | 6.0 |
| 30 | 6.0 |
| 40 | 6.0 |
| 50 | 6.0 |
| 60 | 6.0 |
| 70 | 6.0 |
| 80 | 6.0 |
| 90 | 6.0 |
| 100 | 6.0 |
| 110 | 6.0 |
| 120 | 6.0 |
| 130 | 6.0 |
| 140 | 6.0 |
| 150 | 6.0 |
| 160 | 6.0 |
| 170 | 6.0 |
| 180 | 6.0 |

Weight of Sample

| dry [g] | 30.6 |
|---|---|
| wet [g] | 146.4 |

Figure 49A:
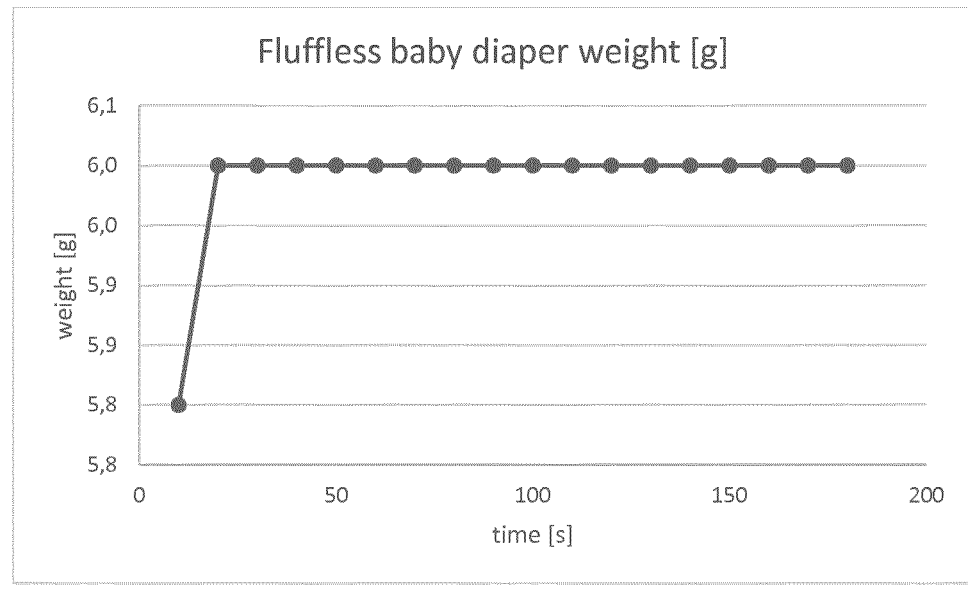
FIG. 49A illustrates dynamic IWHC test results of a "Fluffless" absorbent article test sample, according to a first test run.

These measurements are further illustrated in the graph of FIG. 49A and lead to a IWHCd of 115,8 for the Fluffless baby diaper test sample.

Second Run

| time [s] | weight [g] |
|---|---|
| 10 | 0.0 |
| 20 | 0.0 |
| 30 | 0.0 |
| 40 | 0.0 |
| 50 | 0.0 |
| 60 | 0.0 |
| 70 | 0.4 |
| 80 | 2.2 |
| 90 | 2.7 |
| 100 | 2.7 |
| 110 | 2.7 |
| 120 | 2.7 |
| 130 | 2.7 |
| 140 | 2.7 |
| 150 | 2.7 |
| 160 | 2.7 |
| 170 | 2.7 |
| 180 | 2.7 |
| 190 | 2.7 |
| 200 | 2.7 |
| 210 | 2.7 |
| 220 | 2.7 |
| 230 | 2.7 |
| 240 | 2.7 |
| 250 | 2.7 |
| 260 | 2.7 |
| 270 | 2.7 |

-continued

| time [s] | weight [g] |
|---|---|
| 280 | 2.7 |
| 290 | 2.7 |
| 300 | 2.7 |

Weight of Sample

| dry [g] | 32.7 |
|---|---|
| wet [g] | 217.1 |

Figure 49B:
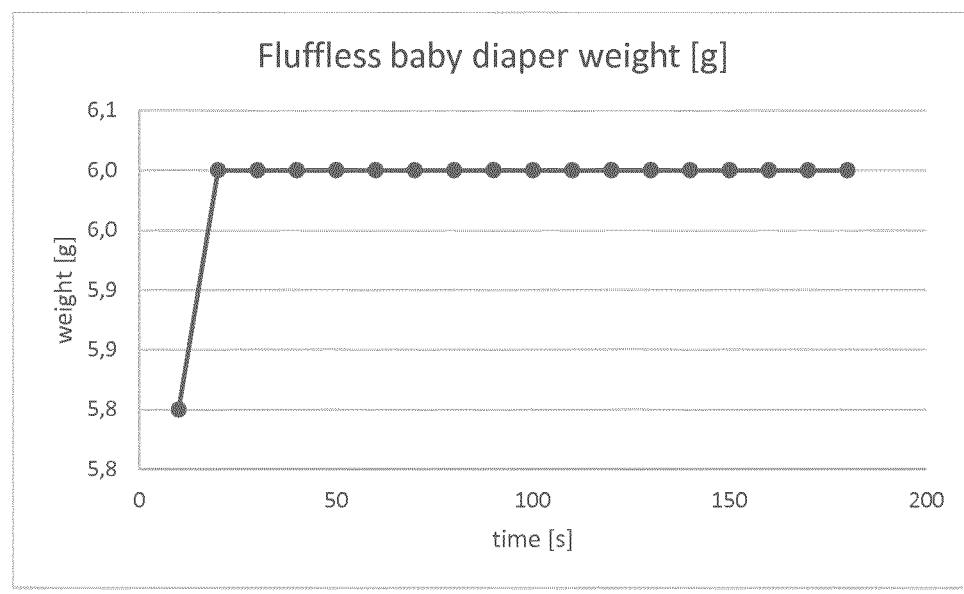
FIG. 49B illustrates dynamic IWHC test results of a "Fluffless" absorbent article test sample, according to a second test run.
Figure 50:
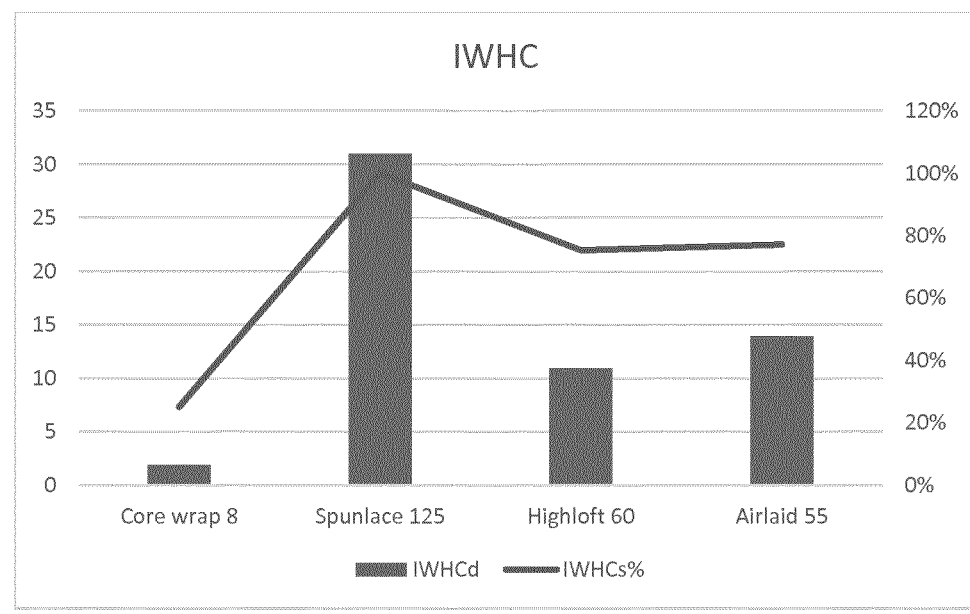

These measurements are further illustrated in the graph of FIG. 49B and lead to a IWHCd of 184,4 for the Flufless baby diaper test sample.

Further embodiments of the absorbent structure are shown in FIGS. 3 to 23 and comprise layers, components and elements as disclosed previously.

Figure 3:
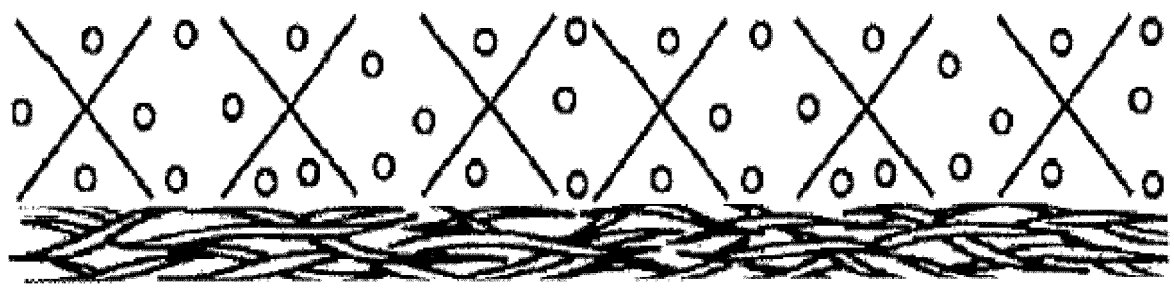
FIGS. 3 to 23 provide cross-sectional schematic illustrations of absorbent structures according to various embodiments of the current invention. More in particular.
Figure 4:
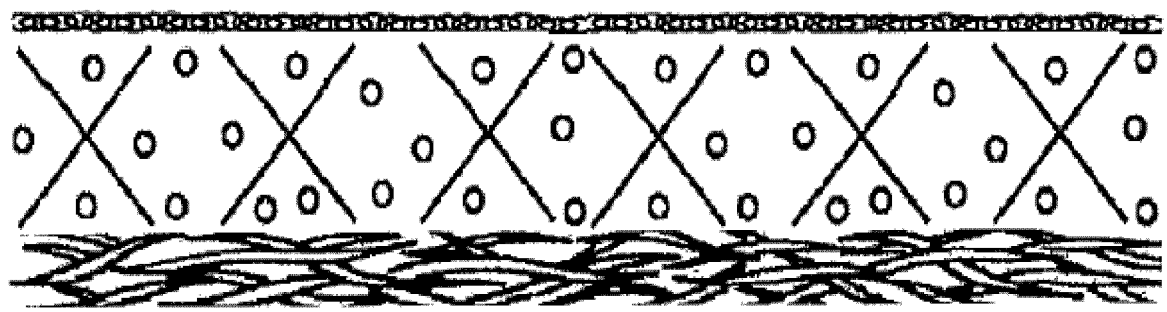
Figure 5:
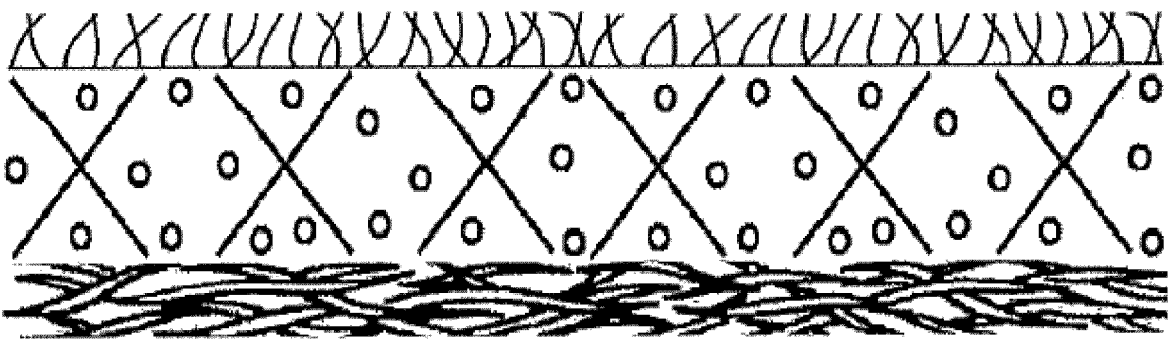
Figure 6:
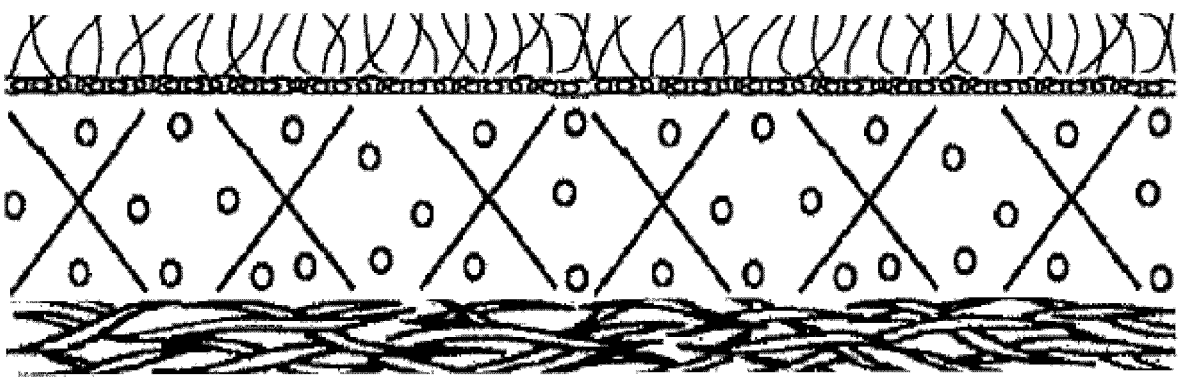
Figure 7:
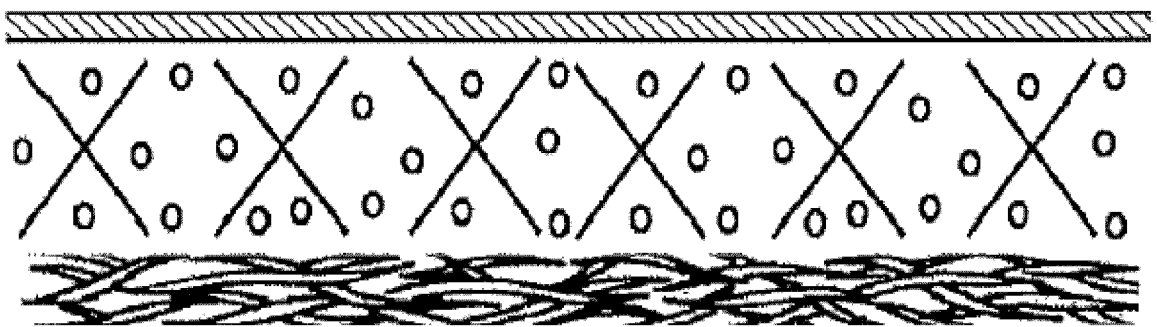
Figure 8:
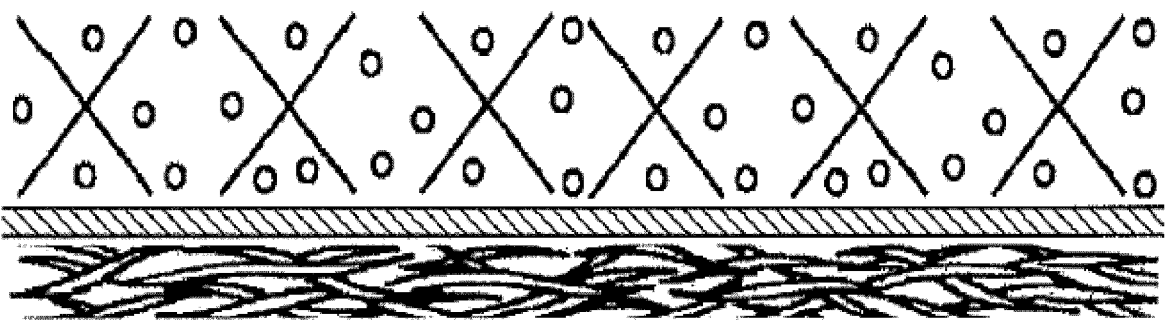
Figure 9:
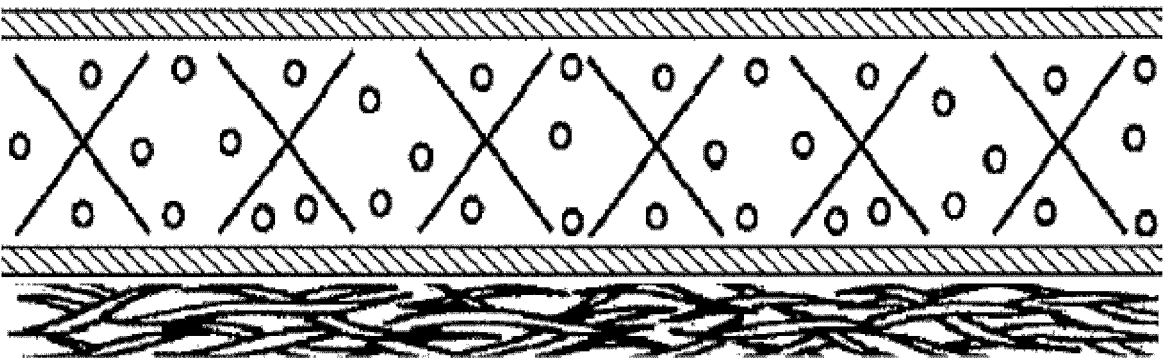
Figure 10:
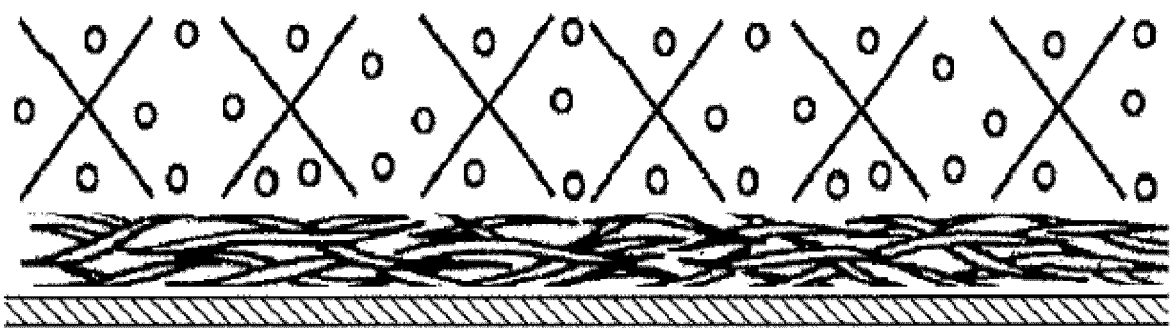
Figure 11:
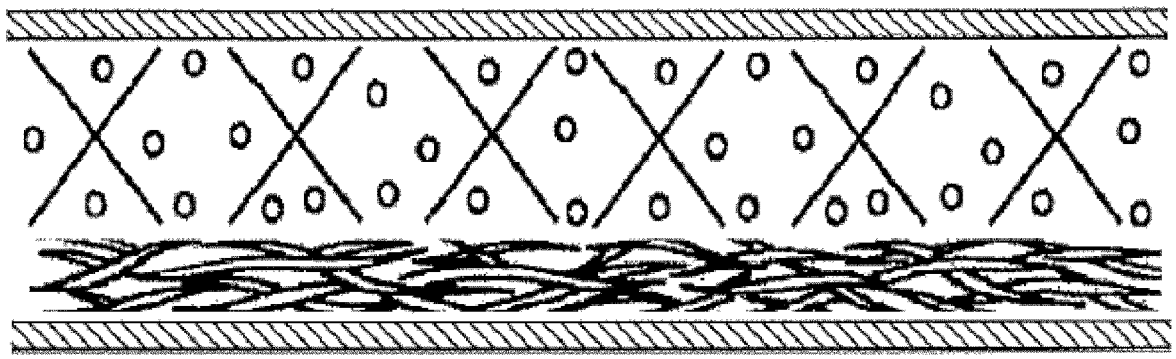
Figure 12:
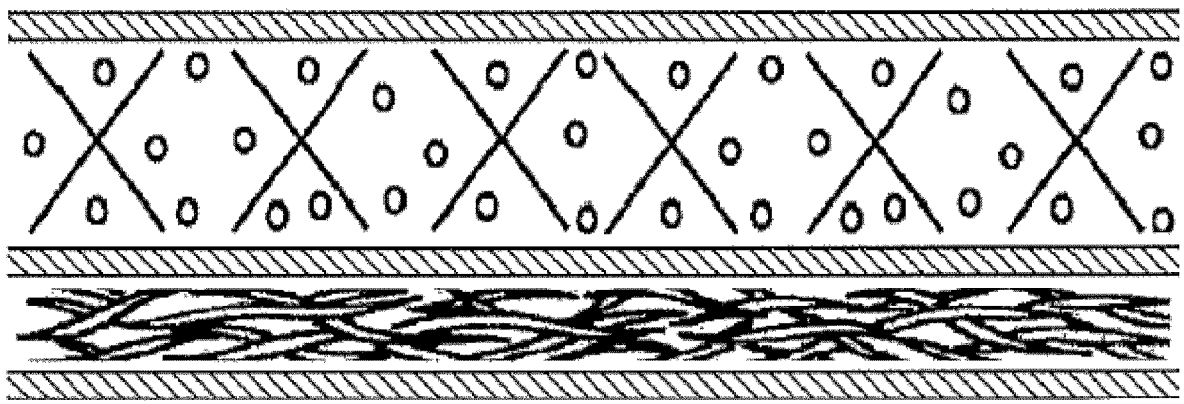
Figure 13:
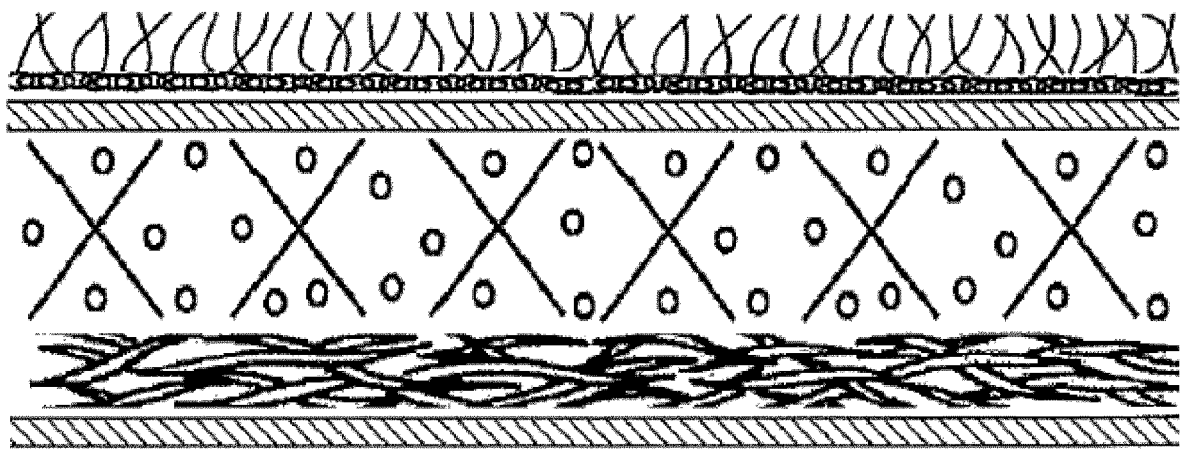
Figure 14:
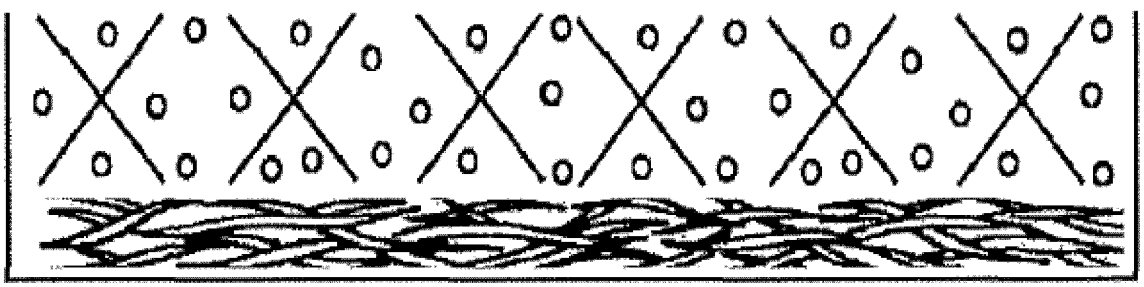
Figure 15:
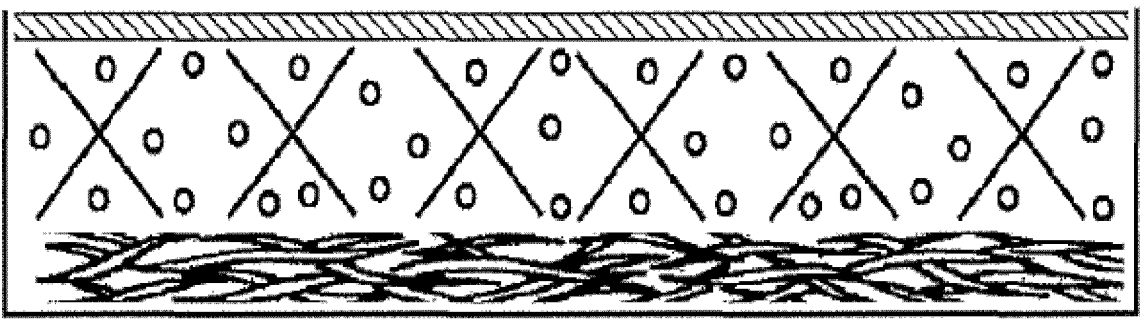
Figure 16:
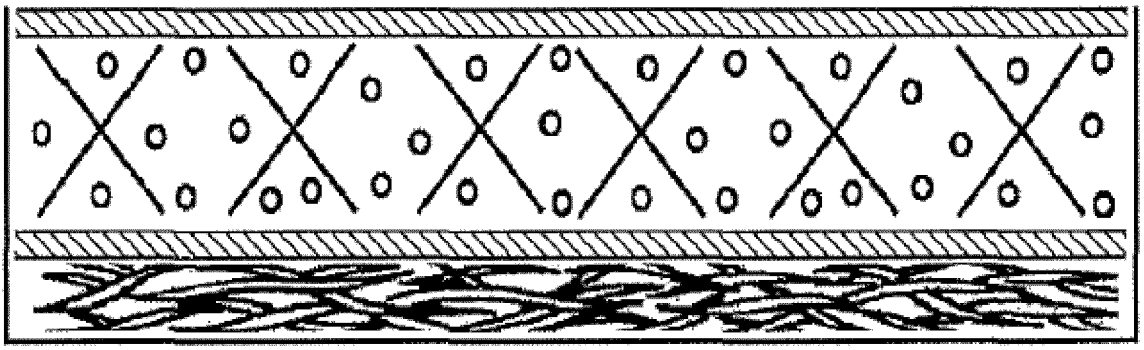
Figure 17:
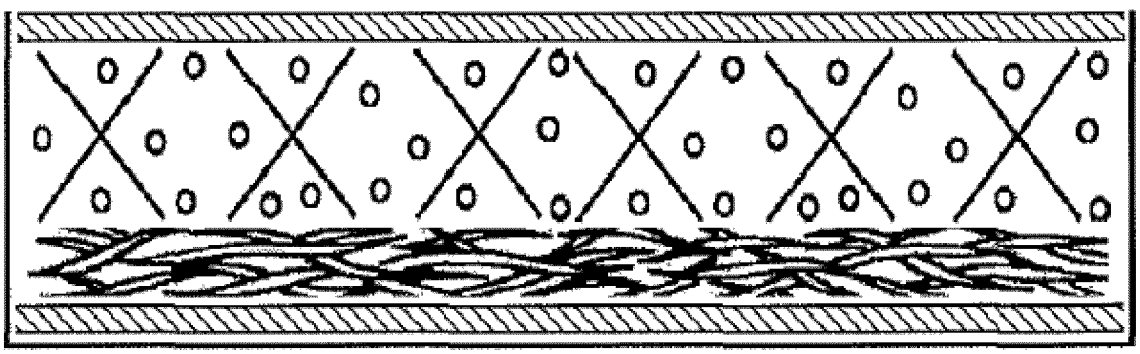
Figure 18:
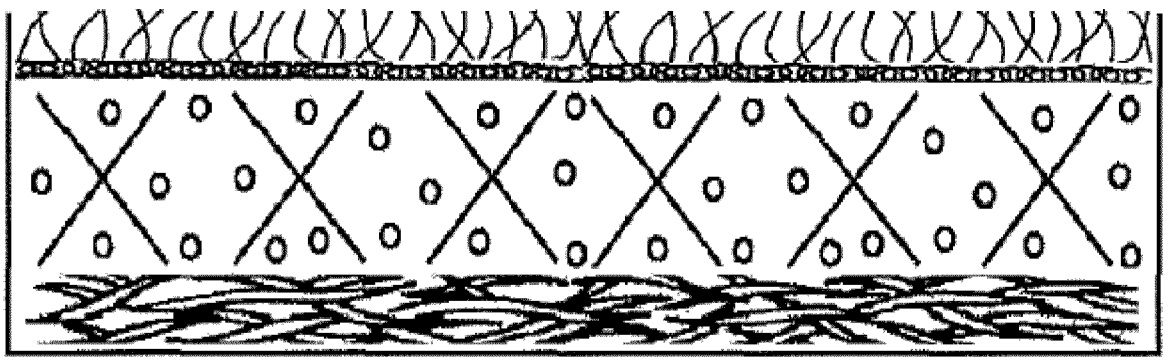
Figure 19:
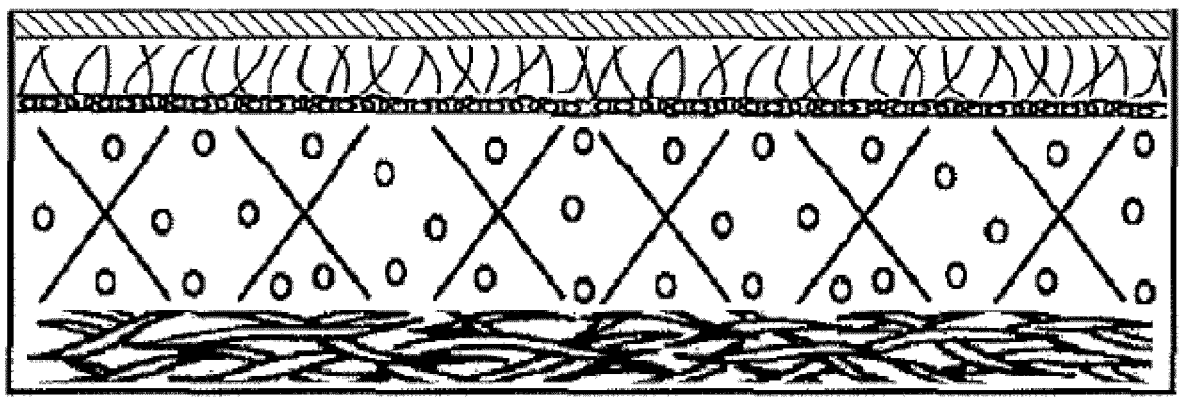
Figure 20:
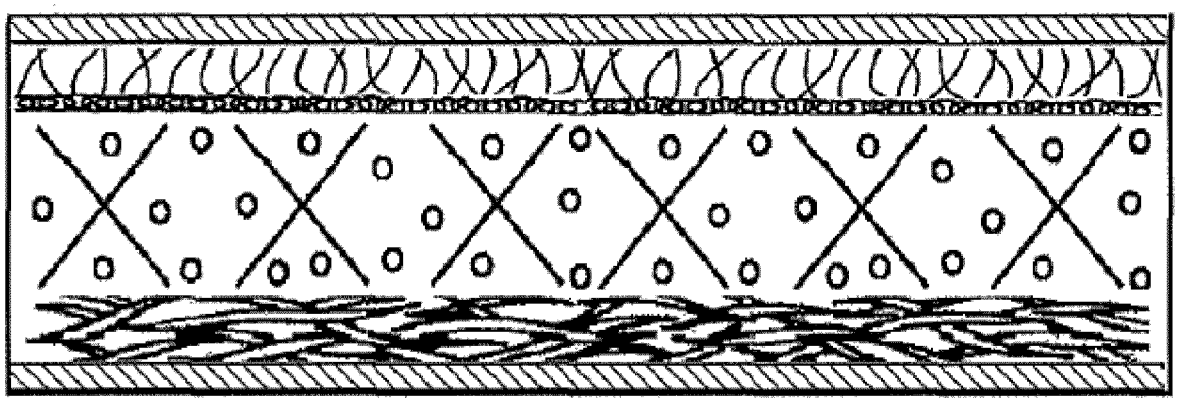
Figure 21:
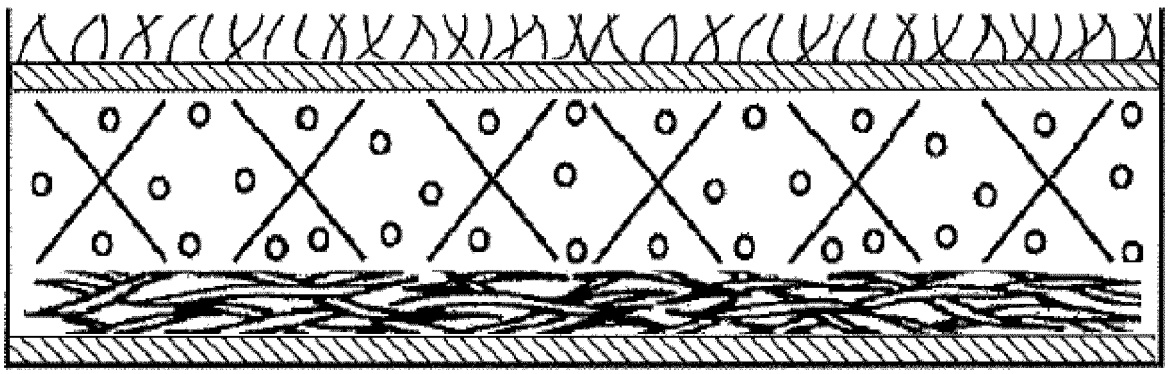
Figure 22:
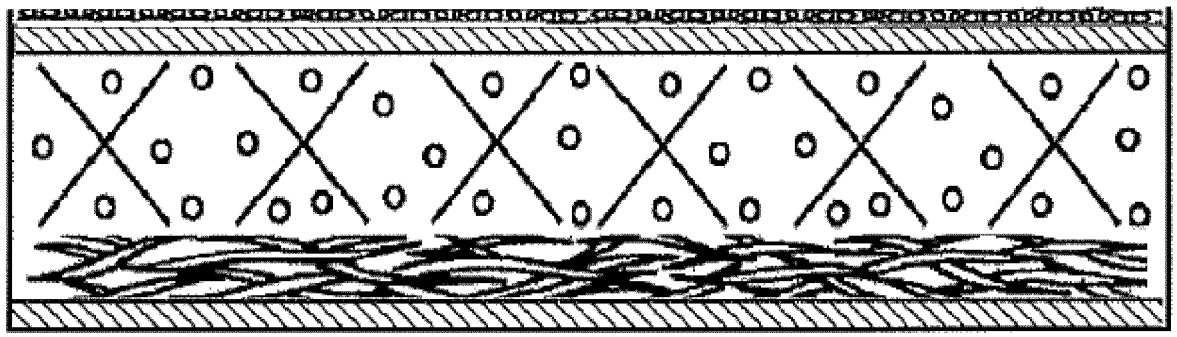
Figure 23:
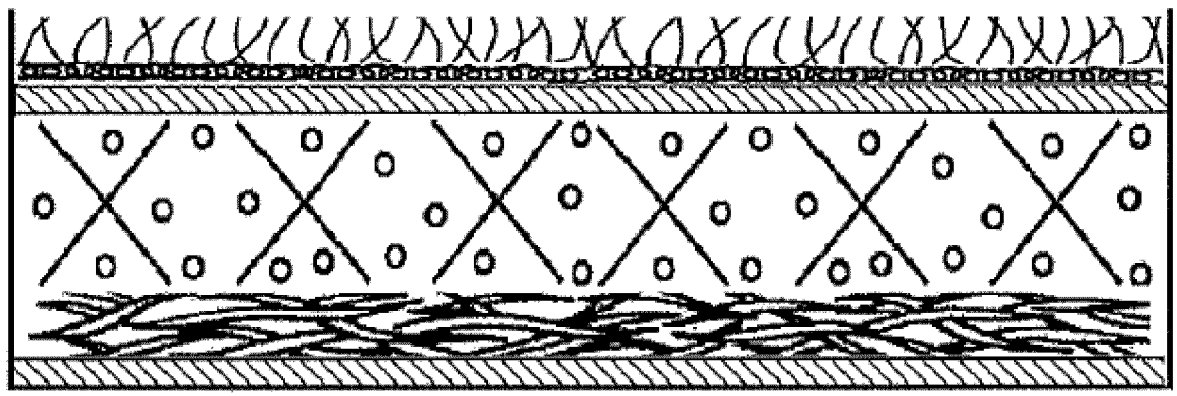

FIG. 3 illustrates a basic embodiment of the absorbent structure of the present invention, comprising an absorbent core, and a release structure positioned in proximity to the absorbent core. The release structure may be positioned directly under the absorbent core, and/or above the absorbent core and/or along the side edges of the absorbent core. Alternatively, one or more additional layers may be positioned between the absorbent core and the release structure as illustrated in the embodiments according to FIG. 8, FIG. 9, FIG. 12 and FIG. 16. The release structure may be positioned directly above the backsheet (not shown) of the absorbent article and/or directly under the topsheet (not shown) of the absorbent article. Alternatively, one or more additional layers may be positioned below the release structure, and thus between the release structure and the backsheet (not shown) and/or topsheet (not shown) of the absorbent article, as illustrated in the embodiments according to FIGS. 10 to 23. In embodiments wherein additional layers are present between the absorbent core and the release structure and/or between the release structure and the backsheet, these additional layers may be unitary with the release structure or they may be components which are separate from the release structure and are bonded or attached to the release structure. FIGS. 4 to 23 illustrate further embodiments of the absorbent structure of the present invention wherein the basic absorbent structure is combined with one or more additional layers according to multiple exemplary configurations.

Although the release structure is illustrated as having a constant thickness, alternative embodiments exist wherein the thickness of the release structures varies along the x-direction and/or y-direction. In FIG. 3 the release structure is illustrated to be a layer which is coextensive with the absorbent core in at least one direction. However, the release structure may be coextensive with the absorbent core in both the x-direction and y-direction of the release structure. Alternatively, the release structure may be smaller than the absorbent core in the x-direction and/or y-direction. Alternatively, the release structure may extend beyond the absorbent core in the x-direction and/or y-direction.

In FIG. 3, the release structure is illustrated to be positioned under the absorbent core and extends continuously over substantially the entire width of the absorbent core. FIGS. 26 to 31 illustrate alternative configurations of the release structure with respect to the absorbent core. Although only the absorbent core and release structure are illustrated in FIGS. 26 to 30, the illustrated configurations may be combined with one or more additional layers in a similar way as illustrated in the embodiments according to FIGS. 4 to 23, mutatis mutandis. Moreover, according to further embodiments of the invention the configuration of the release structure with regard to the absorbent core may be a mirrored configuration of any one of the embodiments as illustrated in FIGS. 3 to 31, wherein the release structure is positioned substantially above the absorbent core in addition to, or alternative to the illustrated embodiments of FIGS. 3 to 31.

Figure 24:
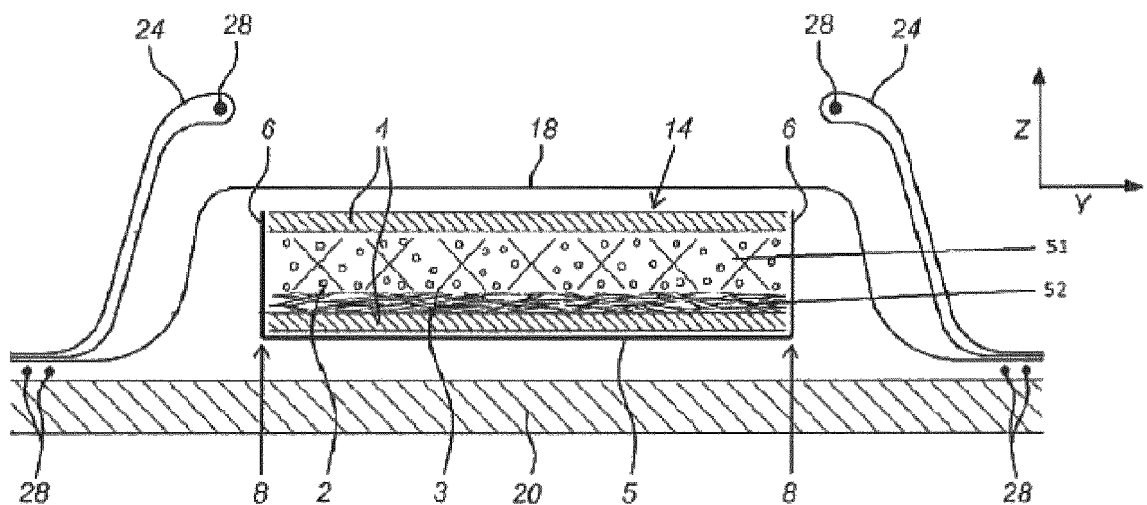
FIG. 24 shows a schematic cross-sectional side view of the absorbent article of FIG. 1 cut along line A-A, hereby showing the components of an absorbent structure according to a preferred embodiment of the current invention.

The absorbent structure can be inserted into e.g. the diaper shown in FIG. 1. This is illustrated by FIG. 24, which shows a cross sectional side view of the crotch section of the diaper 10. The absorbent structure (14) is inserted between the top sheet (18) and the back sheet (20), comprising:
- an upper wrap (4) near the top sheet (18) and a lower wrap (4) near the back sheet (20),
- an absorbent core (51) with fibrous material (3) and absorbent particulate polymer materials (2),
- a release structure (52) and
- a wicking layer (5) and edge barrier (6).

The absorbent structure is preferably transversely positioned in between the cuffs or barriers (24) which comprise elastic members (28), and in between other elastic members (28) such as leg elastics.

Figure 25:
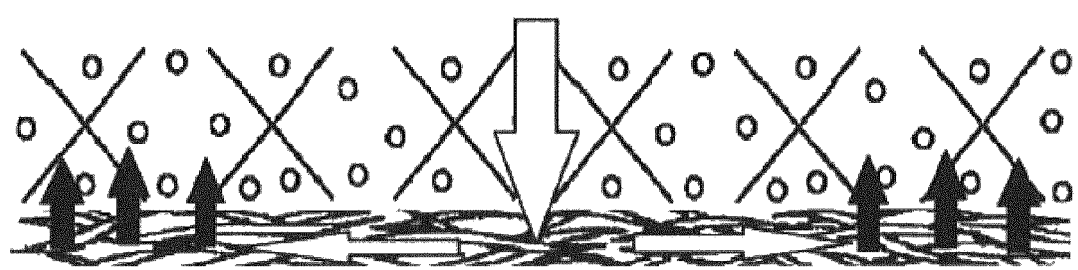
FIG. 25 shows a schematic illustration of the fluid flow in an embodiment of the absorbent structure according to the present invention.

FIG. 25 illustrates the fluid flow in the absorbent structure. A fluid insult comes from above, e.g. from a top sheet and flows centrally downwards (large white arrow). The liquid is allowed to flow through the absorbent core to the release structure, where it is quickly absorbed, gets dispersed sideways, i.e. transversely (smaller white arrows to left and right). The liquid subsequently has the time to be absorbed in non-central zones of the absorbent core (black arrows).

Figure 26:
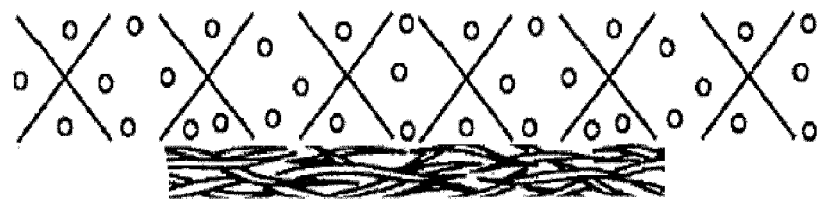
FIGS. 26 to 31 provide cross-sectional schematic illustrations of exemplary configurations of a release structure and absorbent structure according to various embodiments of the current invention. More in particular.

FIG. 26 illustrates an exemplary configuration wherein the release structure is positioned at a central region under the absorbent core. The central region may for example correspond with the crotch region, a part thereof, or another target zone which may be subject to fluid insults passing through the absorbent core. In this embodiment, no release structure is positioned below the side edges of the bottom of the absorbent core. This way, the functionality of the release structure is provided at the central region, while using less release structure material and thus lowering production costs.

Figure 27:
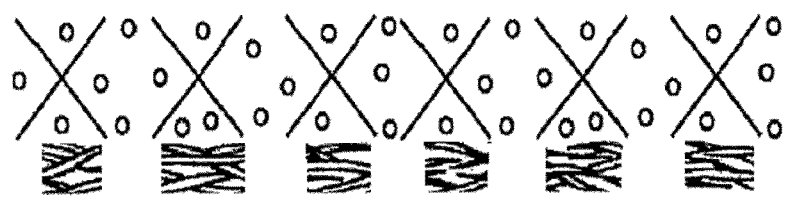

FIG. 27 illustrates a configuration wherein the release structure comprises multiple strips which are positioned below the absorbent core. In this embodiment, the release structure is positioned below the absorbent core and extends over the entire width of the absorbent core, but not in a continuous manner. Alternatively, the strips may be positioned at a central region under the absorbent core in a similar way as illustrated in FIG. 26, mutatis mutandis. The preferred distance between separate strips of the release structure depends on the chosen material of the release structure and the properties of the absorbent core. This way, the functionality of the release structure is provided, while using less release structure material and thus lowering production costs. In a further exemplary configuration, the configurations according to FIG. 26 and FIG. 27 may be combined such that the release structure continuously extends over a central region below the absorbent core and that strips of release structures are positioned below the side edges of the bottom of the absorbent core.

Figure 28:
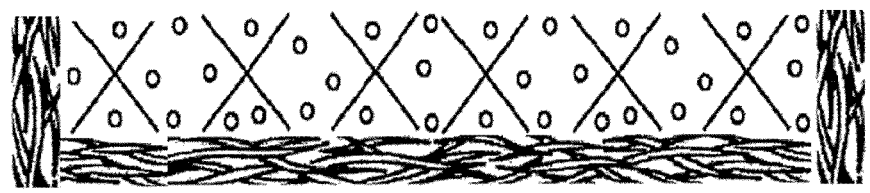

FIG. 28 illustrates a configuration wherein the release structure is positioned below the absorbent core and along the side edges of the absorbent core, and extends along the entire thickness of the absorbent core. This way, the functionality of the release structure is also provided at the side edges of the absorbent core, such that fluids which reach the side edges of the absorbent core can be temporary absorbed by the release structure and subsequently be released to and absorbed by the absorbent core in proximity of the side edges of the absorbent core. In an alternative configuration, the release structure only extends along a part of the entire thickness of the absorbent core.

Figure 29:
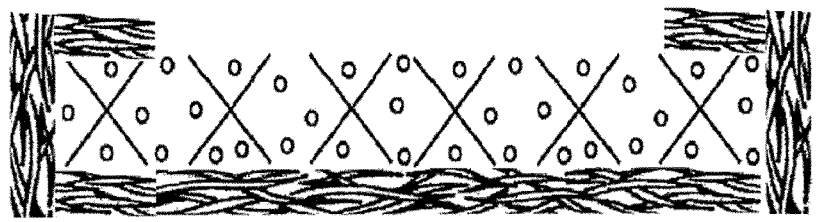

FIG. 29 illustrates a configuration wherein the release structure is positioned below the absorbent core and along the side edges of the absorbent core, extends along the thickness of the absorbent core and is positioned above the absorbent core at the side edges of the absorbent core. The release structure may also further extend along the width of the absorbent core above the absorbent core. This way the absorbent core is partially wrapped by the release structure.

Figure 30:
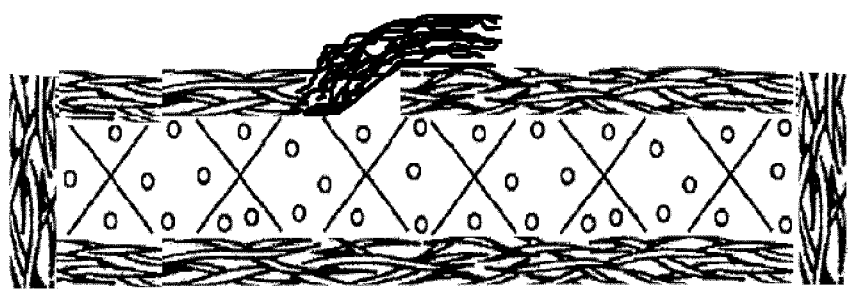
Figure 31:
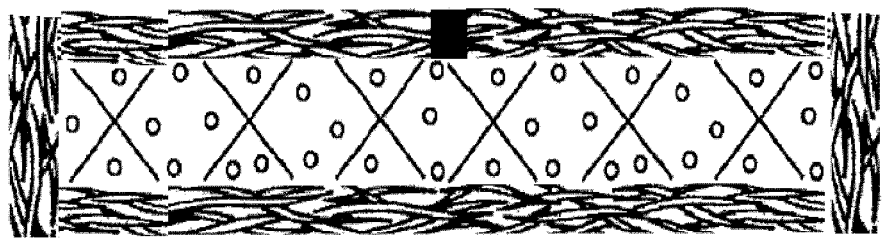

FIGS. 30 and 31 illustrate configurations wherein the release structure is wrapped around the entirety of the absorbent core. In the illustrated embodiment of FIG. 31 the release structure comprises two ends which are attached or bonded to each other above the absorbent core. In alternative embodiments, the two ends may be attached or bonded to each other below the absorbent core and/or at a side of the absorbent core. In the illustrated embodiment of FIG. 30, the release structure comprises two ends which are wrapped respectively over and under each other above the absorbent core to form a closed wrap around the absorbent core. In alternative embodiments, the two ends may be wrapped respectively over and under each other below the absorbent core and/or at a side of the absorbent core.

Figure 32:
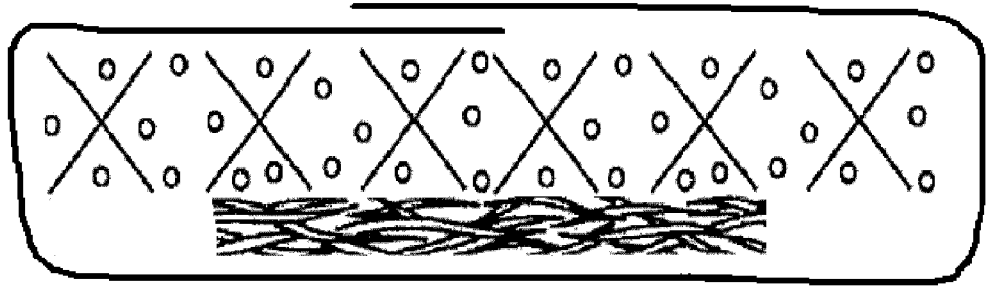
FIG. 32 illustrates an exemplary embodiment wherein an additional core wrap is added to the configuration according to FIG. 26.

FIG. 32 illustrates an embodiment wherein the configuration according to FIG. 26 is supplemented with a core wrap layer which is wrapped around the absorbent core and the release structure. In alternative embodiments, such core wrap layer may be added to any one of the configurations of FIGS. 3, 26 to 31. The core wrap layer may for example be a semi-permeable layer. The core wrap layer does not provide the specific functionality of the release structure, i.e. which does not exhibit a sufficiently high IWHC, but preferably the core wrap layer is cheaper to produce as compared to the release structure. This way, functionality of the release structure may be provided at strategic places, such as the central part below the absorbent core, while keeping production costs relatively low.

Figure 33:
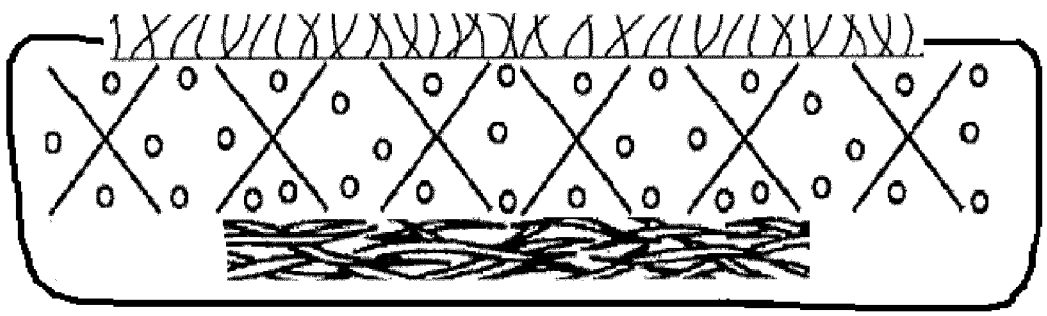
FIG. 33 illustrates a further exemplary embodiment comprising an absorbent core, release structure, core wrap and acquisition layer.

FIG. 33 illustrates an embodiment wherein the configuration according to FIG. 26 is supplemented with a core wrap layer and an acquisition layer. The core wrap layer may be a semi-permeable layer. In addition and/or alternatively the core wrap layer may have properties which a comparable to those of the edge barrier and/or wicking layer. In addition to the illustrated layers, additional layers may be added to the configuration of FIG. 33 in correspondence with any one of the embodiments of FIGS. 3 to 25, mutatis mutandis. In further embodiments, the configuration of the absorbent core and the release structure may be any one of the configurations according to FIGS. 3, 26 to 31.

In any one of the embodiments according to FIGS. 3, 26 to 31 the illustrated release structure may further provide the functionality of a core wrap layer and/or edge barrier and/or wicking layer, either as a unitary layer or as a laminated layer.

Figure 34:
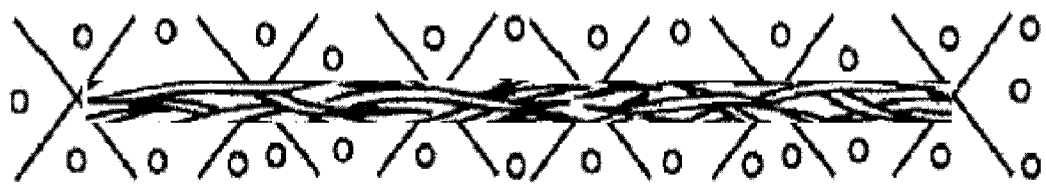
FIG. 34 illustrates an exemplary embodiment wherein the release structure comprises a layer which is positioned within the absorbent core.

FIG. 34 illustrates an exemplary configuration of the absorbent core and release structure wherein the release structure comprises a layer which is positioned within the absorbent core. The dimension of the release structure within the absorbent core may vary in a similar way as described in view of the configurations of FIGS. 26 to 31.

Figure 35:
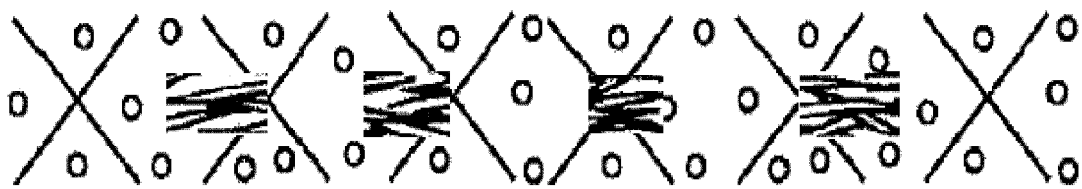
FIG. 35 illustrates an exemplary embodiment wherein the release structure comprises multiple release elements which are positioned within the absorbent core.

FIG. 35 illustrates an exemplary configuration of the absorbent core and release structure wherein the release structure comprises multiple release elements which are positioned within the absorbent core. The release elements may have any shape, and may for example be in the shape of a tube, strip, cube, ball, polygon, layer, polyhedron, etc.

Both configurations as illustrated in FIGS. 34 and 35 may be further combined with any one of the configurations according to FIGS. 26 to 31 or any one of the additional components or layers as illustrated in the embodiments according to FIGS. 3 to 25 and FIGS. 32 and 33.

Whilst the principles of the invention have been set out above in connection with specific embodiments, it is to be understood that this description is merely made by way of example and not as a limitation of the scope of protection which is determined by the appended claims.

The invention claimed is:

1. An absorbent article comprising a liquid pervious topsheet, a liquid impervious backsheet, and an absorbent structure positioned in between said topsheet and said backsheet, wherein the absorbent structure comprises an absorbent core positioned in between the topsheet and the backsheet, an upper core wrap above the absorbent core, a lower core wrap below the absorbent core, and a release structure being positioned in fluid communication with the absorbent core, said absorbent core comprising little to no cellulose fibers and/or fluff pulp and said absorbent core comprising an absorbent polymer material for absorbing and permanently holding fluids received from the topsheet and the release structure, wherein said release structure comprises at least one fibrous substrate structure having the capacity to receive and temporarily hold the fluids in proximity to the absorbent core so that the fluids can subsequently be transferred and released to and absorbed by the absorbent core, wherein at least a part of the release structure is positioned between the absorbent core and the backsheet.

2. The absorbent article according to claim 1, wherein the release structure comprises at least one layer.

3. The absorbent article according to claim 1, wherein the release structure is in contact with the absorbent core.

4. The absorbent article according to claim 1, wherein the absorbent core has a topside facing the topsheet, a bottom side facing the backsheet and at least one side edge between the topside and bottom side, wherein at least part of the release structure is positioned along at least a portion of at least one side edge of the absorbent core.

5. The absorbent article according to claim 1, wherein the release structure is wrapped around the absorbent core.

6. The absorbent article according to claim 1, wherein the absorbent core comprises at least one fibrous substrate layer in which absorbent particulate polymer material is dispersed, embedded and/or immobilized, preferably whereby the weight ratio of the absorbent particulate polymer material versus the substrate layer is at least 20%, and preferably wherein the absorbent core comprises absorbent particles which are dispersed homogenously and/or heterogeneously in the absorbent core.

7. The absorbent article according to claim 1, wherein the release structure comprises cellulose based components.

8. The absorbent article according to claim 1, wherein the weight of the release structure is at least 10 gsm.

9. The absorbent article according to claim 1, wherein the weight of the release structure is between 10 to 300 gsm consisting of natural and/or synthetic fibers.

10. The absorbent article according to claim 1, wherein the release structure comprises a nonwoven, paper, tissue, spunlaced, airlaid, drylaid, wetlaid, spunlaid, meltblown, carded, staple, cellulose, wood pulp, fluff layer and/or substrate.

11. The absorbent article according to claim 1, wherein the release structure exhibits high instantaneous water holding capability, IWHC.

12. The absorbent article according to claim 11, wherein the release structure exhibits a static IWHC percentage, IWHC %, of at least 30%, preferably at least 40%, more preferably at least 50%, and most preferably at least 60%.

13. The absorbent article according to claim 11, wherein the release structure exhibits a dynamic IWHC, IWHCd, of at least 4, preferably at least 10, more preferably at least 20, and most preferably at least 30.

14. The absorbent article according to claim 1, wherein the release structure comprises cellulose-based components and in which the cellulose content is at least 10 gsm.

15. The absorbent article according to claim 1, wherein the absorbent capacity of the release structure is at least 5 g/g.

16. The absorbent article according to claim 1, wherein the absorbent capacity of the release structure is at least 250 g/m$^2$.

17. The absorbent article according to claim 1, wherein the absorbent structure comprises two laterally opposed side edges extending substantially along the x-axis and a front edge and a back edge which extend substantially along the y-axis characterized in that the absorbent structure comprises an edge barrier, which edge barrier is substantially liquid impermeable and/or substantially absorbent particulate polymer material impermeable to prevent sideways leakage of fluid and/or absorbent particulate polymer material from said absorbent structure, said edge barrier being disposed along at least a part of at least one of the side edges, along at least a part of the front edge and/or along at least a part of the back edge, which edge barrier extends along at least a part of the thickness of the absorbent structure and/or in that the absorbent structure comprises a substantially liquid impermeable and/or substantially absorbent particulate polymer material impermeable wicking layer extending along at least a part of the length and width of the absorbent structure, preferably wherein the wicking layer and the edge barrier are made out of one single piece of material.

18. An absorbent article comprising a liquid pervious topsheet, a liquid impervious backsheet, and an absorbent structure positioned in between said topsheet and said backsheet, wherein the absorbent structure comprises an absorbent core positioned in between the topsheet and the backsheet, an upper core wrap above the absorbent core, a lower core wrap below the absorbent core, and a release structure being positioned in fluid communication with the absorbent core, said absorbent core comprising little to no cellulose fibers and/or fluff pulp and said absorbent core comprising an absorbent polymer material for absorbing and permanently holding fluids received from the topsheet and the release structure, wherein said release structure comprises at least one fibrous substrate structure having the capacity to receive and temporarily hold the fluids in proximity to the absorbent core so that the fluids can subsequently be transferred and released to and absorbed by the absorbent core wherein the absorbent core has a topside facing the topsheet, a bottom side facing the backsheet and at least one side edge between the topside and bottom side, wherein at least part of the release structure is positioned along at least a portion of at least one side edge of the absorbent core.

19. The absorbent article according to claim 18, wherein the release structure is wrapped around the absorbent core.

20. An absorbent article comprising a liquid pervious topsheet, a liquid impervious backsheet, and an absorbent structure positioned in between said topsheet and said backsheet, wherein the absorbent structure comprises an absorbent core positioned in between the topsheet and the backsheet, an upper core wrap above the absorbent core, a lower core wrap below the absorbent core, and a release structure being positioned in fluid communication with the absorbent core, said absorbent core comprising little to no cellulose fibers and/or fluff pulp and said absorbent core comprising an absorbent polymer material for absorbing and permanently holding fluids received from the topsheet and the release structure, wherein said release structure comprises at least one fibrous substrate structure having the capacity to receive and temporarily hold the fluids in proximity to the absorbent core so that the fluids can subsequently be transferred and released to and absorbed by the absorbent core wherein at least a part of the release structure is positioned within the absorbent core.

* * * * *